United States Patent [19]

Ohki et al.

[11] 4,395,418
[45] Jul. 26, 1983

[54] PENEM-3-CARBOXYLIC ACID DERIVATIVES

[75] Inventors: Eiji Ohki; Sadao Oida; Akira Yoshida; Teruo Hayashi; Shinichi Sugawara, all of Hiromachi, Japan

[73] Assignee: Sankyo Company Limited, Tokyo, Japan

[21] Appl. No.: 271,010

[22] Filed: Jun. 5, 1981

[30] Foreign Application Priority Data

Jun. 6, 1980 [JP]  Japan ................................ 55-76128
Jun. 23, 1980 [JP]  Japan ................................ 55-84981

[51] Int. Cl.³ .................. A61K 31/425; C07D 499/00
[52] U.S. Cl. .......................... 424/270; 260/245.2 R
[58] Field of Search ................. 260/245.2, 239.1; 424/270

[56] References Cited

U.S. PATENT DOCUMENTS 4,168,314  9/1979  Christensen et al. ........ 260/239 AL
4,347,183  8/1982  Afonso et al. ............... 260/245.2 R Primary Examiner—Nicholas S. Rizzo
Attorney, Agent, or Firm—Frishauf, Holtz, Goodman & Woodward

[57] ABSTRACT

Penem-3-carboxylic acid derivatives of formula (I):

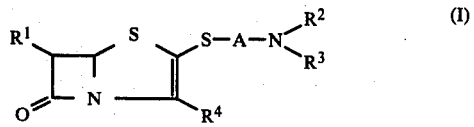

(wherein:
  $R^1$ represents a hydrogen atom, an alkyl group, an alkoxy group, a hydroxyalkyl group, an acyloxyalkyl group, an alkylsulphonyloxyalkyl group, an arylsulphonyloxyalkyl group or a trialkylsilyloxyalkyl group;
  $R^2$ represents a hydrogen atom or an alkyl group;
  $R^3$ represents a hydrogen atom, an amino-protecting group or a group of formula

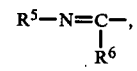

in which $R^5$ and $R^6$ are the same or different and each represents a hydrogen atom or an alkyl group;
  A represents a branched-chain alkylene group; and
  $R^4$ represents a carboxy group or a protected carboxy group)

and pharmaceutically acceptable salts thereof, may be prepared by heating a corresponding phosphorus-ylide compound or by reacting a corresponding azetidin-2-one with a suitable phosphorous acid triester or triamide, and have been found to have excellent antibacterial activity accompanied by a very low acute toxicity.

8 Claims, No Drawings

PENEM-3-CARBOXYLIC ACID DERIVATIVES

BACKGROUND OF THE INVENTION

The present invention relates to a series of new penem-3-carboxylic acid derivatives having valuable antibacterial activity and relatively low toxicity, and to processes for the preparation of these compounds.

The penicillins form a well-known class of antibiotics, which have found considerable use in human and animal therapy for many years. Indeed, benzyl penicillin, which was the first of the antibiotics to come into general therapeutic use, is still widely used today. Chemically, the penicillins have in common a β-lactam-type structure commonly referred to as "penam", which has the following formula:

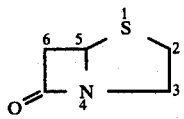

However, although the penicillins still form a valuable weapon in the pharmaceutical armoury the development of new, and often penicillin-resistant, strains of pathogenic bacteria has increasingly made it necessary to search for new types of antibiotic. Recently, some interest has been shown in compounds having a penem structure, that is compounds having a double bond between the carbon atoms in the 2- and 3-positions of the basic penam structure. The penem structure is as follows:

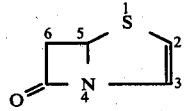

These penam and penem structures form the basis for the semi-systematic nomenclature of the penicillin derivatives and this nomenclature is generally accepted by those skilled in the art throughout the world and is used herein, the numbering system being that illustrated on the above structures.

A variety of penem derivatives has been disclosed in recent years, for example in U.S. Pat. No. 4,168,314 (assigned to Merck & Co.), British Pat. No. 2,013,674 (Ciba Geigy) and British Pat. No. 2,048,261 (Sankyo).

The compound disclosed in United Kingdom Pat. No. 2,048,261, namely 2-[(2-aminoethyl)thio]-6-(1-hydroxyethyl)penem-3-carboxylic acid, was considered to be of considerable interest, since it showed excellent activity against a wide variety of bacteria and thus showed considerable potential for use as an antiobiotic. However, this compound was subsequently shown to have a relatively high acute toxicity.

We have now surprisingly discovered a series of related compounds, which not only have superior antibacterial activity, but which also have a significantly lower acute toxicity.

BRIEF SUMMARY OF INVENTION

The compounds of the present invention have the formula (I):

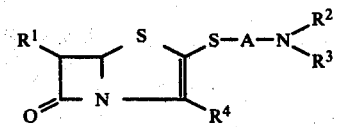

[in which:
$R^1$ represents a hydrogen atom, an alkyl group, an alkoxy group, a hydroxyalkyl group, an acyloxyalkyl group, an alkylsulphonyloxyalkyl group, an arylsulphonyloxyalkyl group or a trialkylsilyloxyalkyl group;
$R^2$ represents a hydrogen atom or an alkyl group;
$R^3$ represents a hydrogen atom, an amino-protecting group or a group of formula

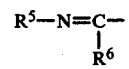

(in which $R^5$ and $R^6$ are the same or different and each represents a hydrogen atom or an alkyl group);
A represents a branched-chain alkylene group; and
$R^4$ represents a carboxy group or a protected carboxy group].

The invention also provides pharmaceutically acceptable salts of the compounds of formula (I).

The invention still further provides a process for preparing compounds of formula (I) and their pharmaceutically acceptable salts, which comprises heating a phosphorus-ylide compound of formula (II):

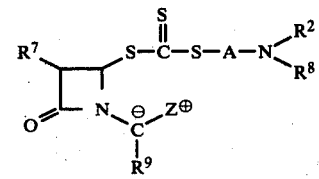

(in which:
$R^2$ and A are as defined above;
$R^7$ represents a hydrogen atom, an alkyl group, an alkoxy group, an acyloxyalkyl group, an alkylsulphonyloxyalkyl group, an arylsulphonyloxyalkyl group or a trialkylsilyloxyalkyl group;
$R^8$ represents an amino-protecting group;
$R^9$ represents a protected carboxy group; and
$Z^+$ represents a tri-substituted phosphonio group or a di-esterified phosphono group accompanied by a cation)
to give a compound of formula (III):

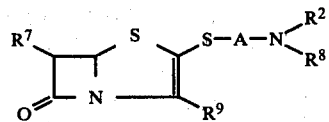

(in which $R^2$, $R^7$, $R^8$, $R^9$ and A are as defined above).

This compound of formula (III) may be the desired final product, in which case it will be separated from the reaction mixture, as described hereafter. On the other hand, if necessary, it may be subjected to one or more of the following steps in any appropriate order and combination:
(a) removal of the carboxy-protecting group from the group $R^9$ to restore a free carboxy group;
(b) removal of a protecting group in the group $R^7$ and/or $R^8$ to restore a hydroxy group, an amino group or an alkylamino group;
(c) where the product obtained contains the group $R^2$—NH—, converting this to a group of formula

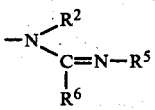

(in which $R^5$, $R^6$ and $R^2$ are as defined above); and
(d) salifying the compound to produce a pharmaceutically acceptable salt of the desired compound of formula (I).

Alternatively, there is provided a process for preparing compounds of formula (I) and their pharmaceutically acceptable salts by reacting an azetidin-2-one derivative of formula (IV):

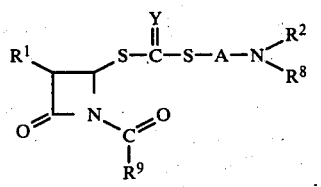 (IV)

(in which $R^1$, $R^2$, $R^8$, $R^9$ and A are as defined above and Y represents an oxygen atom or a sulphur atom) with a phosphorous acid triester or a phosphorous acid triamide, preferably of formula (V):

$$(R^{10})_3P \qquad (V)$$

(in which $R^{10}$ represents an alkoxy group or a dialkylamino group). If desired any combination of the above steps (a)–(d) may then be carried out.

The invention still further provides a pharmaceutical composition comprising a compound of formula (I) or a pharmaceutically acceptable salt thereof in admixture with a pharmaceutically acceptable carrier or diluent.

DETAILED DESCRIPTION OF INVENTION

In the compounds of formula (I), and their pharmaceutically acceptable salts, where $R^1$ represents an alkyl group, it is preferably a lower alkyl group, which may be a straight or branched chain group, for example a methyl, ethyl, propyl, isopropyl, butyl or isobutyl group. Where $R^1$ represents an alkoxy group, this is preferably a lower alkoxy group, which may be straight or branched chain, for example a methoxy, ethoxy, propoxy, isopropoxy, butoxy or isobutoxy group. Where $R^1$ represents a hydroxyalkyl group, this is preferably a lower hydroxyalkyl group, for example a hydroxymethyl, 1-hydroxyethyl, 1-hydroxypropyl, 1-hydroxy-1-methylethyl or 1-hydroxybutyl group.

Where $R^1$ represents an acyloxyalkyl group, the alkyl group is preferably a lower alkyl group, which may be a straight or branched chain group, for example those alkyl groups exemplified above, whilst the acyl group is preferably a lower aliphatic acyl group or an aralkyloxycarbonyl group. Examples of such acyloxyalkyl groups include the acetoxymethyl, 1-acetoxyethyl, 1-propionyloxyethyl, 1-butyryloxyethyl, 1-isobutyryloxyethyl, 1-acetoxypropyl, 1-acetoxy-1-methylethyl, 1-acetoxybutyl, benzyloxycarbonyloxymethyl, 1-benzyloxycarbonyloxyethyl, 1-(p-nitrobenzyloxycarbonyloxy)ethyl, 1-(p-nitrobenzyloxycarbonyloxy)propyl, 1-methyl-1-(p-nitrobenzyloxycarbonyloxy)ethyl or 1-(p-nitrobenzyloxycarbonyloxy)butyl groups.

Where $R^1$ represents an alkylsulphonyloxyalkyl group, the latter alkyl group is preferably a lower alkyl group and examples of such alkylsulphonyloxyalkyl groups include the methanesulphonyloxymethyl, 1-methanesulphonyloxyethyl, 1-propanesulphonyloxyethyl, 1-methanesulphonyloxypropyl, 1-ethanesulphonyloxypropyl, 1-methanesulphonyloxy-1-methylethyl and 1-methanesulphonyloxybutyl groups. Where $R^1$ represents an arylsulphonyloxyalkyl group, the alkyl group is preferably a lower alkyl group and examples of such arylsulphonyloxyalkyl groups include the benzenesulphonyloxymethyl, 1-benzenesulphonyloxyethyl, 1-(p-toluenesulphonyloxy)ethyl, 1-benzenesulphonyloxypropyl, 1-benzenesulphonyloxy-1-methylethyl and 1-benzenesulphonyloxybutyl groups. Where $R^1$ represents a trialkylsilyloxyalkyl group, the latter alkyl group is preferably a lower alkyl group and examples of such trialkylsilyloxyalkyl groups include the trimethylsilyloxymethyl, 1-trimethylsilyloxyethyl, 1-t-butyldimethylsilyloxyethyl, 1-t-butyldimethylsilyloxypropyl, 1-t-butyldimethylsilyloxy-1-methylethyl and 1-t-butyldimethylsilyloxybutyl groups.

$R^2$ represents a hydrogen atom or an alkyl group, which may be a straight or branched chain group and is preferably a lower alkyl group, for example a methyl, ethyl, propyl, isopropyl, butyl or isobutyl group.

Where $R^3$ represents an amino-protecting group, this is preferably an aralkyloxycarbonyl group, for example a benzyloxycarbonyl or p-nitrobenzyloxycarbonyl group. Where $R^3$ represents a group of formula

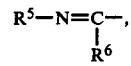

$R^5$ and $R^6$ may each represent a hydrogen atom or an alkyl group, preferably a lower alkyl group such as a methyl, ethyl, propyl or isopropyl group.

A represents a branched chain alkylene group, which is preferably a lower alkylene group and examples of such groups include the 1-methylethylene, 1-ethylethylene, 1-propylethylene, 1-isopropylethylene, 1-butylethylene, 2-methylethylene, 2-ethylethylene, 2-propylethylene, 2-isopropylethylene, 2-butylethylene, 1-methyltrimethylene, 1-ethyltrimethylene, 1-propyltrimethylene, 1-isopropyltrimethylene, 1-butyltrimethylene, 2-methyltrimethylene, 2-ethyltrimethylene, 2-propyltrimethylene, 2-isopropyltrimethylene, 2-butyltrimethylene, 3-methyltrimethylene, 3-ethyltrimethylene, 3-propyltrimethylene, 3-isopropyltrimethylene, 3-butyltrimethylene, 1-methyltetramethylene, 1-ethyltetramethylene, 2-methyltetramethylene, 2-ethyltetramethylene, 3-methyltetramethylene, 3-ethyltetramethylene, 4-methyltetramethylene, 4-ethyltetramethylene, 1,1-dimethylethylene, 1,1-diethylethylene, 2,2-dimethylethylene, 2,2-diethylethylene, 1,1-dimethyltrimethylene, 1.1 diethyltrimethylene, 2,2-dimethyltrimethylene, 2,2-diethyltrimethylene, 3,3-dimethyltrimethylene, 3,3-diethyltrimethylene, 1,2-dimethyltrimethylene, 1,3-dimethyltrimethylene, 2,3- dimethyltrimethylene, 1,1-dimethyltetramethylene, 1,1-diethyltetramethylene, 2,2-dimethyltetramethylene, 2,2-diethyltetramethylene, 3,3-dimethyltetramethylene, 3,3-diethyltetramethylene, 4,4-dimethyltetramethylene, 4,4-diethyltetramethylene, 1,2-dimethyltetramethylene, 1,2-diethyltetramethylene, 1,3-dimethyltetramethylene, 1,3-diethyltetramethylene, 2,3-dimethyltetramethylene, 1,4-dimethyltetramethylene, 2,4-dimethyltetramethylene, 3,4-dimethyltetramethylene and 1,4-diethyltetramethylene groups.

$R^4$ which represents a carboxy group or a protected carboxy group, is preferably a group of formula

—COOR$^{4'}$, where $R^{4'}$ represents a hydrogen atom or a carboxy-protecting group. Examples of suitable carboxy-protecting groups include: straight or branched chain lower alkyl groups, e.g. the methyl, ethyl, propyl, isopropyl, butyl, isobutyl or t-butyl groups; lower haloalkyl groups, such as the 2-iodoethyl, 2,2-dibromoethyl or 2,2,2-trichloroethyl groups; a lower alkoxymethyl group, such as a methoxymethyl, ethoxymethyl, propoxymethyl, isopropoxymethyl, butoxymethyl or isobutoxymethyl group; a lower aliphatic acyloxymethyl group, such as an acetoxymethyl, propionyloxymethyl, butyryloxymethyl, isobutyryloxymethyl or pivaloyloxymethyl group; a lower 1-alkoxycarbonyloxyethyl group, such as a 1-methoxycarbonyloxyethyl, -ethoxycarbonyloxyethyl, 1-propoxycarbonyloxyethyl, 1-isopropoxycarbonyloxyethyl, 1-butoxycarbonyloxyethyl or 1-isobutoxycarbonyloxyethyl group; an aralkyl group, such as a benzyl, p-methoxybenzyl, o-nitrobenzyl or p-nitrobenzyl group; a benzhydryl group; or a phthalidyl group.

Particularly preferred compounds of formula (I) are those compounds and their salts in which:

$R^1$ represents a methoxy group or a 1-hydroxyethyl group;

$R^2$ represents a hydrogen atom or a $C_1$–$C_2$ alkyl group;

$R^3$ represents a hydrogen atom, a formimidoyl group or an acetimidoyl group;

A represents an ethylene, trimethylene or tetramethylene group having in its carbon chain one or two methyl and/or ethyl substituents (for example the 1-methylethylene, 2-methylethylene, 1-ethylethylene, 2-ethylethylene, 1,1-dimethylethylene, 2,2-dimethylethylene, 1,2-dimethylethylene, 1-methyltrimethylene, 2-methyltrimethylene, 3-methyltrimethylene, 1-ethyltrimethylene, 2-ethyltrimethylene, 3-ethyltrimethylene, 1,1-dimethyltrimethylene, 2,2-dimethyltrimethylene, 3,3-dimethyltrimethylene, 1,3-dimethyltrimethylene, 2,3-dimethyltrimethylene, 1-methyltetramethylene, 2-methyltetramethylene, 3-methyltetramethylene, 4-methyltetramethylene, 1-ethyltetramethylene, 2-ethyltetramethylene, 3-ethyltetramethylene, 4-ethyltetramethylene, 1,1-dimethyltetramethylene, 1,2-dimethyltetramethylene, 1,3-dimethyltetramethylene, 2,3-dimethyltetramethylene, 1,4-dimethyltetramethylene, 2,4-dimethyltetramethylene or 3,4-dimethyltetramethylene groups; and $R^4$ represents a carboxy group or a pivaloyloxymethoxycarbonyl group.

The most preferred compounds of the invention are those compounds of formula (I) and their salts in which:

$R^1$ represents a hydroxyethyl group;

$R^2$ represents a hydrogen atom or a $C_1$–$C_2$ alkyl group, most preferably a hydrogen atom;

$R^3$ represents a hydrogen atom, a formimidoyl group or an acetimidoyl group, most preferably a hydrogen atom;

$R^4$ represents the group

—COOR$^{4''}$, where $R^{4''}$ represents a hydrogen atom, or pivaloyloxymethyl group, a sodium atom or a potassium atom, most preferably a hydrogen atom or a sodium atom; and a represents an ethylene or trimethylene group, most preferably an ethylene group, whose carbon chain has one or two, most preferably one, methyl substituents in the α- or β- positions, most preferably the α-position.

The following is a list of preferred compounds of the present invention:

(1) 2-(2-Amino-1-methylethylthio)penem-3-carboxylic acid.

(2) 2-(2-Aminopropylthio)penem-3-carboxylic acid.

(3) 2-(2-Amino-1-methylethylthio)-6-methoxypenem-3-carboxylic acid.

(4) 2-(2-Aminopropylthio)-6-methoxypenem-3-carboxylic acid.

(5) 2-(2-Amino-1-ethylethylthio)-6-methoxypenem-3-carboxylic acid.

(6) 2-(3-Amino-1-methylpropylthio)-6-methoxypenem-3-carboxylic acid.

(7) 2-(4-Amino-1-methylbutylthio)-6-methoxypenem-3-carboxylic acid.

(8) 2-(2-Amino-1-methylethylthio)-6-(1-hydroxyethyl)-penem-3-carboxylic acid.

(9) p-Nitrobenzyl 6-(1-t-butyldimethylsilyloxyethyl)-2-[1-methyl-2-(p-nitrobenzyloxycarbonylamino)ethylthio]-penem-3-carboxylate.

(10) 2-(2-Aminopropylthio)-6-(1-hydroxyethyl)penem-3-carboxylic acid.

(11) p-Nitrobenzyl 6-(1-t-butyldimethylsilyloxyethyl)-2-[2-(p-nitrobenzyloxycarbonylamino)propylthio]-penem-3-carboxylate.

(12) 2-(2-Amino-1-ethylethylthio)-6-(1-hydroxyethyl)-penem-3-carboxylic acid.

(13) 2-(2-Aminobutylthio)-6-(1-hydroxyethyl)penem-3-carboxylic acid.

(14) 2-(2-Amino-1,1-dimethylethylthio)-6-(1-hydroxyethyl)penem-3-carboxylic acid.

(15) 2-(2-Amino-2-methylpropylthio)-6-(1-hydroxyethyl)penem-3-carboxylic acid.

(16) 2-(2-Amino-1-methylpropylthio)-6-(1-hydroxyethyl)penem-3-carboxylic acid.

(17) 2-(3-Amino-1-methylpropylthio)-6-(1-hydroxyethyl)penem-3-carboxylic acid.

(18) 2-(3-Amino-2-methylpropylthio)-6-(1-(hydroxyethyl)penem-3-carboxylic acid.

(19) 2-(3-Aminobutylthio)-6-(1-hydroxyethyl)penem-3-carboxylic acid.

(20) 2-(3-Amino-1,1-dimethylpropylthio)-6-(1-hydroxyethyl)penem-3-carboxylic acid.

(21) 2-(3-Amino-2,2-dimethylpropylthio)-6-(1-hydroxyethyl)penem-3-carboxylic acid.

(22) 2-(3-Amino-3-methylbutylthio)-6-(1-hydroxyethyl)penem-3-carboxylic acid.

(23) 2-(3-Amino-1-methylbutylthio)-6-(1-hydroxyethyl)penem-3-carboxylic acid.

(24) 2-(4-Amino-1-methylbutylthio)-6-(1-hydroxyethyl)penem-3-carboxylic acid.
(25) 2-(4-Amino-2-methylbutylthio)-6-(1-hydroxyethyl)penem-3-carboxylic acid.
(26) 2-(4-Amino-1-methylpentylthio)-6-(1-(hydroxyethyl)penem-3-carboxylic acid.
(27) 2-(2-Formimidoylamino-1-methylethylthio)-6-methoxypenem-3-carboxylic acid.
(28) 2-(2-Formimidoylaminopropylthio)-6-methoxypenem-3-carboxylic acid.
(29) 2-(3-Formimidoylamino-1-methylpropylthio)-6-methoxypenem-3-carboxylic acid.
(30) 2-(4-Formimidoylamino-1-methylbutylthio)-6-methoxypenem-3-carboxylic acid.
(31) 2-(2-Formimidoylamino-1-methylethylthio)-6-(1-hydroxyethyl)penem-3-carboxylic acid.
(32) 2-(2-Acetimidoylamino-1-methylethylthio)-6-(1-hydroxyethyl)penem-3-carboxylic acid.
(33) 2-(2-Formimidoylaminopropylthio)-6-(1-hydroxyethyl)penem-3-carboxylic acid.
(34) 2-(2-Acetimidoylaminopropylthio)-6-(1-hydroxyethyl)penem-3-carboxylic acid.
(35) 2-(2-(Formimidoylamino-1-ethylethylthio)-6-(1-hydroxyethyl)penem-3-carboxylic acid.
(36) 2-(3-Formimidoylamino-1-methylpropylthio)-6-(1-hydroxyethyl)penem-3-carboxylic acid.
(37) 2-(4-Formimidoylamino-1-methylbutylthio)-6-(1-hydroxyethyl)penem-3-carboxylic acid.
(38) Pivaloyoxymethyl 2-(2-amino-1-methylethylthio)-6-methoxypenem-3-carboxylate.
(39) Pivaloyloxymethyl 2-(2-amino-1-methylethylthio)-6-(1-hydroxyethyl)penem-3-carboxylate.
(40) Pivaloyloxymethyl 2-(2-aminopropylthio)-6-(1-hydroxyethyl)penem-3-carboxylate.
(41) Pivaloyloxymethyl 2-(3-amino-1-methylpropylthio)-6-(1-hydroxyethyl)penem-3-carboxylate.
(42) Pivaloyloxymethyl 2-(4-amino-1-methylbutylthio)-6-(1-hydroxyethyl)penem-3-carboxylate.
(43) 6-(1-Hydroxyethyl)-2-(2-methylamino-1-methylethylthio)penem-3-carboxylic acid.
(44) 2-(2-Ethylamino-1-methylethylthio)-6-(1-hydroxyethyl)penem-3-carboxylic acid.
(45) 6-(1-Hydroxyethyl)-2-(1-methyl-3-methylaminopropylthio)penem-3-carboxylic acid.
(46) 2-(3-Ethylamino-1-methylpropylthio)-6-(1-hydroxyethyl)penem-3-carboxylic acid.
(47) p-Nitrobenzyl 6-(1-hydroxyethyl)-2-[1-methyl-2-(p-nitrobenzyloxycarbonylamino)ethylthio]penem-3-carboxylate.
(48) p-Nitrobenzyl 6-(1-hydroxyethyl)-2-[2-(p-nitrobenzyloxycarbonylamino)propylthio]penem-3-carboxylate.

In the case of those compounds listed above which are acids, that is to say Compounds No. 1–8, 10, 12–37 and 43–46, the sodium and potassium salts are also preferred. Compound No. 8 and its salts are most preferred, especially in the (5R,6S)-1'-(R)-configuration.

Because of the presence of asymmetric carbon atoms in the compounds of the invention, they can exist in the form of various stereoisomers, both optical isomers and geometric isomers. All of these isomers are represented herein by a single formula but it will be understood that the present invention envisages both the individual isomers as well as mixtures thereof. The preferred compounds are those in which the carbon atom at the 5-position is in the same configuration as the corresponding atom in the natural penicillins, that is to say the R-configuration and hence the (5R,6S) and (5R,6R) isomers are particularly preferred. When the group $R^1$ (at the 6- position of the penem system) is a 1-substituted alkyl group (e.g. a 1-hydroxyethyl or 1-t-butyldimethylsilyloxyethyl group), the preferred configuration of the substituent is again the R-configuration.

The compounds of the invention may be prepared by the following methods.

Method A

In this Method, compounds of formula (III):

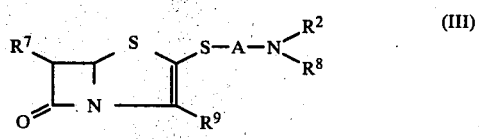

(in which $R^2$, $R^7$, $R^8$, $R^9$ and A are as defined above) are prepared by heating a phosphorus-ylide compound of formula (II):

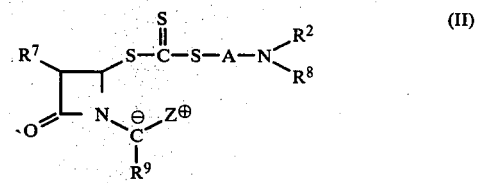

(in which $R^2$, $R^7$, $R^8$, $R^9$, A and $Z^+$ are as defined above).

The reaction may be carried out in the presence or absence of a solvent. Where a solvent is employed, its nature is not critical, provided that it has no adverse effect upon the reaction. Suitable solvents include: ethers, such as dioxan; and aromatic hydrocarbons, such as benzene, toluene or xylene. The temperature to which the phosphorus-ylide compound (II) is heated is also not critical, but we prefer to carry out this reaction at a temperature of from 100° to 200° C. and, if necessary, in an atmosphere of an inert gas, such as nitrogen or argon. Where no solvent is employed, the reaction may also be conducted in an evacuated reaction vessel. The time required for the reaction will depend upon the nature of the starting materials and upon the reaction temperature, but in general a period of from 5 to 12 hours will suffice.

When the reaction is complete, the desired compound of formula (III) may be recovered from the reaction mixture by conventional means. For example, one suitable recovery system comprises distilling the solvent from the reaction mixture under reduced pressure, adding a mixture of ethyl acetate and hexane to the resulting residue, filtering off the precipitates so produced and finally distilling off the solvent from the filtrate to give the desired compound. If necessary, the compound of formula (III) thus obtained may be further purified by conventional means, for example by recrystallization, preparative thin layer chromatography or column chromatography. It is also possible to subject the compound of formula (III) to other reactions, as described hereafter, to prepare other compounds of formula (I).

Method B

Compounds of formula (III), as defined above, and the corresponding compounds in which $R^7$ has been replaced by $R^1$ may be prepared by reacting an azetidinone derivative of formula (IV):

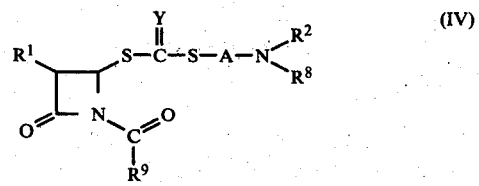

with a phosphorous acid ester or amide of formula (V):

$$(R^{10})_3P \qquad (V)$$

in which $R^1$, $R^2$, $R^8$, $R^9$, $R^{10}$, A and Y are as defined above.

Suitable phosphorous acid esters include trimethyl phosphite and triethyl phosphite and a suitable phosphorous acid amide is tris(dimethylamino)phosphine. The amount of phosphorous acid ester or amide (V) is preferably from 2 to 20 equivalents per equivalent of azetidinone derivative (IV).

The reaction is preferably carried out in the presence of a solvent, the nature of which is not critical, provided that it has no adverse effect upon the reaction. Suitable solvents include: alcohols, such as methanol, ethanol, propanol and isopropanol; ethers, such as tetrahydrofuran or dioxan; esters, such as ethyl acetate or butyl acetate; aromatic hydrocarbons, such as benzene or toluene; halogenated hydrocarbons, such as chloroform or methylene chloride; fatty acid dialkylamides, such as dimethylformamide or dimethylacetamide; and nitriles, such as acetonitrile. It is possible to employ a single one of these solvents or a mixture of any two or more thereof.

The reaction temperature is also not critical, but we generally prefer to carry out the reaction at a temperature within the range from ambient temperature to 150° C., more preferably from 50° C. to 150° C. The time required for the reaction will depend mainly upon the nature of the starting materials and on the reaction temperature and is generally from 5 hours to 4 days.

Where this reaction temperature is relatively low, for example if it is between ambient temperature and 90° C., the simple reaction of the azetidinone derivative (IV) with the phosphorous acid ester or amide (V) may produce an ylide compound of formula (VI):

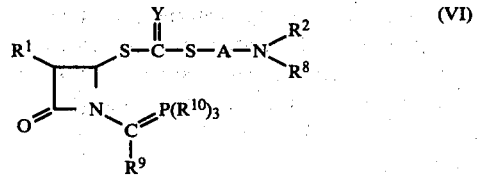

(in which $R^1$, $R^2$, $R^8$, $R^9$, $R^{10}$, A and Y are as defined above). If this ylide compound is formed, then it should be heated, without the need for any intermediate purification, to give the desired penem-3-carboxylic acid derivative. The heating temperature is preferably from 100° to 150° C. and the time required for this reaction is generally from 4 to 48 hours.

The compounds prepared as described by the Methods A and B may then be subjected to any one or more of the following reactions: removal of hydroxy-protecting groups, removal of amino-protecting groups, removal of carboxy-protecting groups, replacement of the group represented by $R^8$ by a group of formula

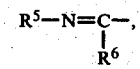

and salification.

Removal of carboxy-protecting groups

The protected carboxy group represented by $R^9$ in the compound obtained by Method A or B may be converted to a free carboxy group by conventional means. The reaction required to remove the protecting group will vary depending upon the nature of the protecting group, but any method known in the art may be employed.

For example, where the protecting group is a halogenated alkyl group, an aralkyl group or a benzhydryl group, it may be removed by contacting the compound produced in Method A or B with a reducing agent. In the case of halogenated alkyl groups, (e.g. 2,2-dibromoethyl or 2,2,2-trichloroethyl groups), a preferred reducing agent is a combination of zinc with acetic acid. In the case of aralkyl groups (e.g. benzyl or p-nitrobenzyl groups) or the benzhydryl group, a preferred reducing agent is a catalytic reducing agent (e.g. palladium on charcoal) in the presence of hydrogen, or an alkali metal sulphide (e.g. sodium sulphide or potassium sulphide). The reaction will normally be carried out in the presence of a solvent, the nature of which is not critical, provided that it has no adverse effect upon the reaction. Preferred solvents are alcohols (such as methanol or ethanol), ethers (such as tetrahydrofuran or dioxan), fatty acids (such as acetic acid) or a mixture of one or more of these organic solvents with water. The reaction temperature will normally be within the range from 0° C. to about ambient temperature. The time required for the reaction will vary depending upon the reagents and the reaction temperature, but the reaction is normally complete within from 5 minutes to 12 hours.

After completion of the reaction, the product may be recovered from the reaction mixture by conventional means, e.g. by filtering off insolubles, washing the organic solvent phase with water and drying it and then distilling off the solvent. If necessary, the product may be further purified by such conventional means as recrystallization, preparative thin layer chromatography or column chromatography.

Removal of hydroxy- and amino-protecting groups

When $R^7$ in the compound prepared in Method A or B represents an acyloxyalkyl group or a trialkylsilyloxyalkyl group and/or the group $R^8$ represents an amino-protecting group, the protecting groups may, if necessary, be removed by conventional means to restore a free hydroxy group, a free amino group or (where $R^2$ represents an alkyl group) a free alkylamino group. These reactions may take place before, after or together with the removal of the carboxy-protecting group in $R^9$.

Compounds in which $R^1$ represents a hydroxyalkyl group may be prepared by removing the hydroxy-protecting group (e.g. acyl group or trialkylsilyl group) from the compound of formula (III). Where the protected hydroxy group is a lower aliphatic acyloxy group (e.g. an acetoxy group), the protecting group may be removed by treating the corresponding compound with a base in the presence of an aqueous solvent. There is no particular limitation on the nature of this solvent, and any solvent commonly used in hydrolysis may be employed. However, we particularly prefer water or a mixture of water with an organic solvent, such as an alcohol (e.g. methanol, ethanol or propanol) or an ether (e.g. tetrahydrofuran or dioxan). The base employed is also not particularly critical, provided that it does not affect other parts of the compound, particularly the β-lactam ring. Preferred bases are alkali metal carbonates, such as sodium carbonate or potassium carbonate. Equally, the reaction temperature is not critical, but we prefer a temperature of from 0° C. to about ambient temperature, in order to control side reactions. The time required for the reaction will vary depending upon the nature of the starting materials and upon the reaction temperature, but the reaction will normally be complete within a period of from 1 to 6 hours.

Where the group represented by $R^7$ is an aralkyloxycarbonyloxyalkyl group [e.g. a 1-benzyloxycarbonyloxyethyl group or a 1-(p-nitrobenzyloxycarbonyloxy)ethyl group], the protecting group may be removed by contacting the corresponding compound with a reducing agent. The reducing agent and reaction conditions which may be employed are the same as those which may be employed for the removal of aralkyl groups from the protected carboxy group $R^9$. Accordingly, by choosing appropriate protecting groups, it is possible simultaneously to remove protecting groups from $R^7$ and $R^9$.

Where the group represented by $R^7$ is a trialkylsilyloxyalkyl group (e.g. a 1-t-butyldimethylsilyloxyethyl group), the protecting group may be removed by treating the corresponding compound with tetrabutylammonium fluoride in a suitable solvent, the nature of which is not critical, provided that it has no adverse effect upon the reaction. Suitable solvent are ethers, such as tetrahydrofuran or dioxan. The reaction is normally carried out at about room temperature and will normally require from 10 to 18 hours.

Compounds of formula (I) in which $R^3$ represents a hydrogen atom, i.e. amino and alkylamino compounds, may be prepared by removing the aralkyloxycarbonyl group (e.g. benzyloxycarbonyl or p-nitrobenzyloxycarbonyl) represented by $R^8$ in the compound of formula (III). This removal is preferably effected by reduction. The reducing agents and reaction conditions which may be employed are the same as those which may be employed for the removal of aralkyl groups from the protected carboxy group represented by $R^9$. Accordingly, by choosing appropriate protecting groups, it is possible simultaneously to remove protecting groups from $R^8$ and $R^9$.

Conversion of amino group to imidoyl group

A compound of formula (I) in which $R^3$ represents a group of formula

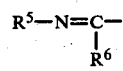

(in which $R^5$ and $R^6$ are as defined above) may be prepared by contacting the corresponding compound in which $R^3$ represents a hydrogen atom, i.e. an amino or alkylamino compound, with an imide ester of formula (VII):

(in which $R^5$ and $R^6$ are as defined above and $R^{11}$ represents an alkyl group, for example a methyl, ethyl, propyl or isopropyl group).

The reaction is preferably effected in the presence of a solvent, the nature of which is not critical, however, where the starting material is a compound in which $R^3$ represents a hydrogen atom and $R^4$ represents a free carboxy group, we prefer to employ as the solvent a phosphate buffer solution which maintains the pH of the reaction mixture at a value of about 8. The reaction is preferably carried out at a relatively low temperature, e.g. from 0° C. to about ambient temperature, and the time required for the reaction will normally be from 10 minutes to 2 hours.

Salification

Carboxylic acids of formula (I), that is to say compounds in which $R^4$ represents a free carboxy group, can be converted to their corresponding pharmaceutically acceptable salts. Examples of such salts include salts with metals (particularly the lithium, sodium, potassium, calcium or magnesium salts), ammonium salts and organic amine salts (particularly the cyclohexylammonium, diisopropylammonium or triethylammonium salts), preferably the sodium or potassium salts. The salification reaction may be carried out by methods well-known in the art, either before or after separating the corresponding carboxylic acid from the reaction mixture.

The desired compound prepared as described above may be recovered from its reaction mixture by conventional means and, if necessary, further purified by recrystallization, preparative thin layer chromatography or column chromatography.

PREPARATION OF STARTING MATERIALS

Starting material for Method A

The phosphorus-ylide compound of formula (II), which is the starting material for Method A, may be prepared as illustrated by the following reaction scheme, which also summarizes the preparation of the final products from this phosphorus-ylide compound.

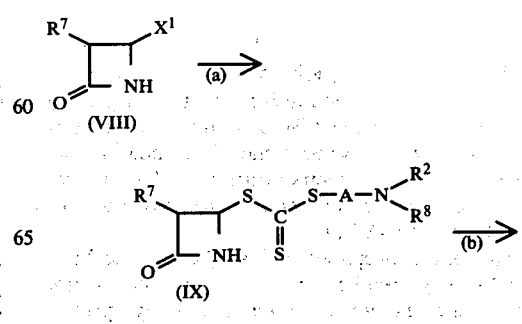

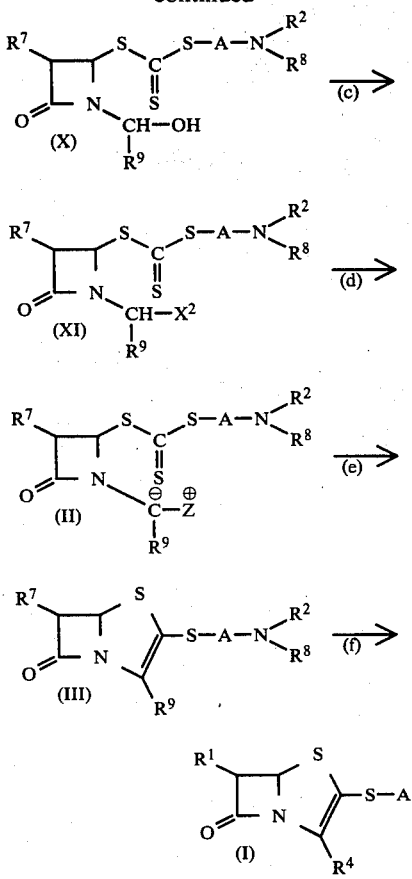

salt may itself be prepared by reacting a mercaptan compound of formula (XIII):

$$\underset{R^8}{\overset{R^2}{>}}N-A-SH \qquad (XIII)$$

(in which $R^2$, $R^8$ and A are as defined above) with carbon disulphide and a alkali metal hydroxide (e.g. sodium hydroxide or potassium hydroxide) or an alkali metal alkoxide (e.g. sodium methoxide, sodium ethoxide or potassium ethoxide).

The reaction in step (a) of the compound of formula (VIII) with the compound of formula (XII) is preferably effected in the presence of a solvent, the nature of which is not critical, provided that it has no adverse effect upon the reaction. Preferred solvents include: water, alcohols, such as methanol, ethanol or propanol, ketones, such as acetone or methyl ethyl ketone; fatty acid dialkylamides, such as dimethylformamide or dimethylacetamide; and mixtures of one or more of the above organic solvents with water. The molar ratio of the compound of formula (VIII) to the compound of formula (XII) is preferably from 1:1 to 1:1.5. The reaction temperature is not critical, although we prefer to carry out the reaction at a temperature of from −20° C. to 50° C. The time required for the reaction will depend mainly on the nature of the starting materials and the reaction temperature, but the reaction will normally be complete within from 10 minutes to 2 hours.

The resulting compound of formula (IX) may be recovered from the reaction mixture by conventional means, for example as follows: adding a water-immiscible organic solvent (such as ethyl acetate) and water to the reaction mixture, separating the organic layer; washing the organic layer with water and then drying it with a drying agent; and finally, distilling off the solvent from the organic layer to give the desired compound. The resulting compound may, if necessary, be further purified by conventional means, for example by recrystallization, preparative thin layer chromatography or column chromatography.

Step (b) of the above reaction scheme comprises reacting the compound of formula (IX) with a glyoxylic acid ester of formula (XIV):

(in which $R^9$ is as defined above). This reaction is preferably effected in the presence of a solvent, the nature of which is not critical, provided that it has no adverse effect upon the reaction. Preferred solvents include: ethers, such as tetrahydrofuran or dioxan; aromatic hydrocarbons, such as benzene or toluene; fatty acid dialkylamides, such as dimethylformamide or dimethylacetamide, and mixtures of these organic solvents. This addition reaction may occasionally be accelerated by the presence of a base, for example an organic base (e.g. triethylamine, diisopropylethylamine or pyridine) or a sodium aluminium silicate molecular sieve. The reaction temperature is not critical, but we generally prefer to employ a temperature from ambient to about 100° C. If a base is used, the reaction is preferably effected at about ambient temperature. On the other hand, if no base is used, the reaction is preferably effected at the In the above formulae, $R^1$, $R^2$, $R^3$, $R^4$, $R^7$, $R^8$, $R^9$, A and $Z^+$ are as defined above. $X^1$ represents an acyloxy group (e.g. an acetoxy, propionyloxy or benzoyloxy group) an alkylsulphonyl group (e.g. a methanesulphonyl or ethanesulphonyl group) or an arylsulphonyl group (e.g. a benzenesulphonyl or p-toluenesulphonyl group). $X^2$ represents a halogen atom such as a chlorine, bromine or iodine atom. Examples of the groups represented by $R^7$ and $R^9$ include those exemplified for $R^1$ and $R^4$, other than those groups including free hydroxy grups or free carboxy groups, respectively. Examples of groups represented by $R^8$, the amino-protecting group, include aralkyloxycarbonyl groups, such as the benzyloxycarbonyl and p-nitrobenzyloxycarbonyl groups. Where $Z^+$ represents a trisubstituted phosphonio group, this is preferably a tri(lower alkyl)phosphonio group (e.g. a tributylphosphonio group) or a triarylphosphonio group (e.g. a triphenylphosphonio group); where $Z^+$ represents a di-esterified phosphono group accompanied by a cation, it is preferably a diethylphosphono group accompanied by a lithium or sodium ion.

Step (a) of the above reaction scheme comprises reacting the compound of formula (VIII) with a trithiocarbonic acid alkali metal salt of formula (XII):

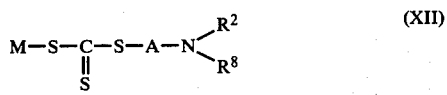

(in which M represents an alkali metal atom, for example a sodium or potassium atom, and $R^2$, $R^8$ and A are as defined above). This trithiocarbonic acid alkali metal reflux temperature of the solvent employed and, if necessary, in an atmosphere of an inert gas, such as nitrogen. The time required for the reaction will depend upon the nature of the starting materials and the reaction temperature, but it will generally be complete within from 1 to 6 hours.

After completion of the reaction, the desired compound may be recovered from the reaction mixture by conventional means, for example filtering insolubles from the reaction mixture, washing the filtrate with water and drying it over a drying agent, and finally distilling off the solvent and excess reagents to give the desired compound which may, if necessary, be further purified by such conventional means as recrystallization, preparative thin layer chromatography or column chromatography.

Step (c) of the reaction scheme comprises halogenating the resulting compound of formula (X) to give a compound of formula (XI). This reaction may simply be carried out by contacting the compound of formula (X) with an halogenating agent in the presence of a solvent. The nature of the halogenating agent to be employed is not critical, but we prefer to use thionyl halides (such as thionyl chloride or thionyl bromide), phosphorus oxyhalides (such as phosphorus oxychloride), phosphorus halides (such as phosphorus pentachloride or phosphorus pentabromide) or oxalyl halides (such as oxalyl chloride). The reaction is preferably carried out in the presence of a base, suitably an organic base, such as triethylamine, diisopropylethylamine, pyridine or lutidine. There is no particular limitation on the nature of the solvent to be employed, provided that it has no adverse effect upon the reaction. Suitable solvents include ethers, such as tetrahydrofuran or dioxan. The reaction temperature is also not critical, but we prefer to carry out the reaction at a relatively low temperature (e.g. from $-15°$ C. to about ambient temperature) in order to control side reactions. If necessary, the reaction may be conducted under an atmosphere of an inert gas, such as nitrogen. The time required for the reaction will depend upon the nature of the starting materials and on the reaction temparature, but the reaction will generally be complete within a period of from 10 to 30 minutes. After completion of the reaction, the resulting compound of formula (XI) may be recovered from the reaction mixture by conventional means, for example by distilling off the solvent and excess reagent; the resulting compound may conveniently be employed in the next step without any further purification.

The halogen atom represented by $X^2$ in the resulting compound of formula (XI) thus obtained may be converted to any other halogen atom by known methods. For example, the chlorine compound [$X^2$ is chlorine in compound (XI)] may be converted to the corresponding bromine or iodine compound by treating it with an inorganic bromide or iodide (e.g. lithium bromide or potassium iodide) in an organic solvent, such as diethyl ether.

Step (d) prepares the phosphorus-ylide compound of formula (II) by reacting the compound of formula (XI) with a phosphine compound or with a phosphorous ester and a base in the presence of a solvent.

Suitable phosphine compounds which may be employed in the reaction include tri(lower alkyl)phosphines (such as tributylphosphine) and triarylphosphines (such as triphenylphosphine). Suitable phosphorous ester compounds include tri(lower alkyl) phosphites (such as triethyl phosphite) and alkali metal salts of di(lower alkyl) phosphite esters, such as sodium dimethyl phosphite. When a phosphine compound is used, the base is preferably an organic base, such as triethylamine, diisopropylethylamine pyridine or 2,6-lutidine. On the other hand, when a phosphorous diester is used, the base is preferably an alkali metal hydride (such as sodium hydride) or a lower alkyllithium (such as butyllithium). There is no particular limitation on the nature of the solvent to be employed, provided that it has no adverse effect upon the reaction and preferred solvents include: aliphatic hydrocarbons, such as hexane or cyclohexane; ethers, such as tetrahydrofuran or dioxan; aromatic hydrocarbons, such as benzene or toluene; and fatty acid dialkylamides such as dimethylformamide or dimethylacetamide. The reaction temperature is also not critical and we generally prefer to carry out the reaction at a temperature of from $30°$ to $100°$ C., if necessary, in an atmosphere of an inert gas, such as nitrogen. The time required for the reaction will depend upon the nature of the starting materials and upon the reaction temperature, but it is generally from 1 to 50 hours.

When the reaction is complete, the desired phosphorus-ylide compound may be recovered from the reaction mixture by conventional means, for example as follows: a water-immiscible organic solvent (such as ethyl acetate) and water are added to the reaction mixture; the organic layer is separated, washed with water and dried with a drying agent; and then the solvent is distilled off to give the desired compound. This compound may, if desired, be further purified by such conventional means as recrystallization, preparative thin layer chromatography or column chromatography.

Steps (e) and (f) of the above reaction scheme involve conversion of the phosphorus-ylide compound of formula (II) to the compound of formula (III) and, if desired, to the compound of formula (I), as described under Method A.

The 4-acyloxyazetidin-2-one or 4-sulphonylazetidin-2-one compound of formula (VIII), which is the starting material for the process illustrated in the above reaction scheme may be prepared, for example, as shown in the following reaction scheme:

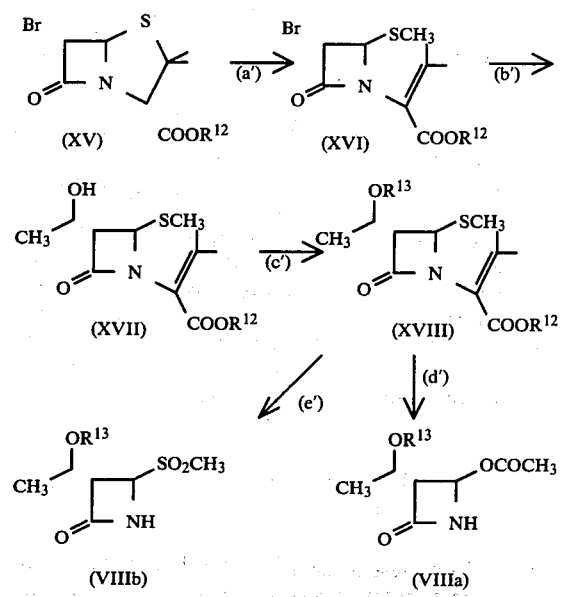

In the above formulae, $R^{12}$ represents a carboxy-protecting group, such as an alkyl group (e.g. methyl, ethyl or t-butyl) or an aralkyl group (e.g. benzyl), and; $R^{13}$ represents a hydroxy-protecting group, for example a p-nitrobenzyloxycarbonyl group or a t-butyldimethylsilyl group.

Following the reaction scheme shown above, a known 6α-bromopenicillanic acid ester of formula (XV) [J. P. Clayton, J. Chem. Soc. (C), 2123 (1969)] is treated with trimethyloxonium tetrafluoroborate and a base (such as basic alumina), in turn, to give the ring-opened compound of formula (XVI). This compound of formula (XVI) is, in turn, treated with a Grignard reagent (such as methylmagnesium bromide) or with a dialkylcopper lithium (such as dimethylcopper lithium) followed by treatment with acetaldehyde, to give the compound of formula (XVII). Alternatively, it is treated first with zinc in the presence of a dialkylaluminium halide (such as diethylaluminium chloride) to give an enolate anion, which is then reacted with acetaldehyde to give the compound (XVII). The hydroxy group at the 1'-position of the compound (XVII) is then protected by conventional means to give the compound (XVIII). This compound (XVIII) is either treated with mercuric acetate in acetic acid and oxidized with potassium permanganate to give one of the desired starting materials (VIIIa) or is oxidized with potassium periodate in the presence of potassium permanganate to give the 4-methanesulphonylazetidin-2-one (VIIIb).

When the compound of formula (XVII) is prepared from the compound of formula (XVI) by the method described above, the configuration of the 1'-position of the hydroxyethyl group at the 3-position of the azetidinone ring is mainly the S-configuration. If this compound is treated with an organic acid in the presence of triphenylphosphine and diethylazodicarboxylate, there is obtained an acyloxy compound in which the 1'-position is in the R-configuration (i.e. the configuration of the 1'-position has been inverted). This compound may then be converted back to the hydroxy compound by treatment with a solution of an alkali metal alkoxide in an alcohol (e.g. sodium methoxide in methanol) by conventional methods, in which case the R-configuration is retained at the 1'-position. This R-compound may then be used in succeeding processes to give a final product having the R-configuration.

Also, it is possible to react the compound of formula (XVI) with aliphatic aldehydes other than acetaldehyde to give compounds having a 1-hydroxyalkyl group other than the 1-hydroxyethyl group at the 3-position of the azetidinone ring. Preparation of other starting materials may be effected in a similar manner.

Preparation of starting materials for Method B

The compound of formula (IV), which is the starting material for Method B may be prepared by reacting an azetidinone derivative of formula (XIX):

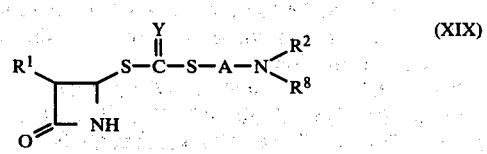

[in which $R^1$, $R^2$, $R^8$, Y and A are as defined above, which may be synthesized by the methods described in the following literature: S. Oida, A. Yoshida, T. Hayashi, N. Takeda, T. Nishimura and E. Ohki J. Antiobiotics, 33, 107, (1980); I. Ernest, J. Gosteli, C. W. Greengrass, W. Holick, D. E. Jackman, H. R. Pfaendler and R. B. Woodward, J. Am. Chem. Soc., 100, 8214 (1978)] with from 1 to 4 equivalents of an alkoxalyl halide of formula (XX):

(in which $R^9$ is as defined above and $X^2$ represents a halogen atom, preferably chlorine or bromine), in the presence of a solvent and of from 1 to 4 equivalents of an organic base. The product thus obtained may be recovered and, if desired, further purified by conventional means.

The compounds of the invention have been shown to have excellent antibacterial activities against a wide range of pathogenic microorganisms. By the agar plate dilution method, excellent antibacterial activity has been demonstrated against both gram-positive microorganisms (such as *Staphylococcus aureus* and *Bacillus subtilis*) and gram-negative microorganisms (such as *Escherichia coli*, *Shigella flexneri*, *Klebsiella pneumoniae*, *Proteus vulgaris* and *Pseudomonas aeruginosa*). The minimal inhibitory concentrations of one of the compounds of the invention, namely (5R,6S)-2-(2-amino-1-methylethylthio)-6-[(R)-1-hydroxyethyl]penem-3-carboxylic acid (Compound No. 8) and a previously disclosed compound, (5R,6S)-2-(2-aminoethylthio)-6-[(R)-1-hydroxyethyl]penem-3-carboxylic acid, are shown in μg/ml) in the following Table against a variety of microorganisms.

TABLE

| Microorganism | Compound A | Compound B |
| --- | --- | --- |
| *Escherichia coli* NIHJ | 0.1 | 0.4 |
| *Escherichia coli* 609 | 0.1 | 0.8 |
| *Shigella flexneri* 2A | 0.05 | 0.8 |
| *Klebsiella pneumoniae* 806 | 0.1 | 0.8 |
| *Klebsiella pneumoniae* 846 | 0.2 | 0.8 |
| *Salmonella enteritidis* G | 0.1 | 0.8 |

Compound A is the compound of the invention and Compound B is the known compound. It can be seen that the compound of the invention has significantly better activity than does the known compound, even though the activity of the known compound is itself extremely good. Moreover, when Compounds A and B were injected intravenously into mice, Compound B killed them at a dose of 500–1000 mg/kg, whereas Compound A showed no adverse effect at a dose of 1000 mg/kg, thus demonstrating a far weaker acute toxicity.

Accordingly, the compounds of the invention may be used for the treatment of diseases caused by many pathogenic microorganisms. For this purpose, the compounds of the invention may be administered orally (e.g. in the form of tablets, capsules, granules, powders or syrups) or parenterally (e.g. by intravenous injection or intramuscular injection). The dose will vary depending upon the age, body weight and condition of the patient and on the route and type of administration but, in general, the compounds of the invention may be administered in a daily dose of from 250 to 3000 mg for adults, either as a single dose or as divided doses.

The preparation of compounds of the invention is further illustrated by the following Examples, and the preparation of certain of the starting materials used in these Examples is illustrated by the following Preparations.

EXAMPLE 1

(3S, 4R)3-[(R)-1-t-Butyldimethylsilyloxyethyl]-4-[1-methyl-2-p-nitrobenzyloxycarbonylaminoethylthio(thiocarbonyl)]thioazetidin-2-one 168 mg (0.59 mmole) of 1-methyl-2-(p-nitrobenzyloxycarbonylamino)ethanethiol were added to a solution of 12.5 mg (0.57 mmole) of metallic sodium in 4 ml of methanol at −10° C., and then the mixture was stirred for 5 minutes. 45 mg (0.59 mmole) of carbon disulphide were added to the resulting solution at the same temperature, followed by stirring for 10 minutes. Then 154 mg (0.54 mmole) of (3R, 4R)-4-acetoxy-3-[(R)-1-t-butyldimethylsilyloxyethyl]azetidin-2-one were added to the solution at the same temperature. The bath temperature was slowly elevated to 0° C. over a period of about 1 hour. After completion of the reaction, the reaction solution was made slightly acidic by the addition of a drop of acetic acid, diluted with ethyl acetate, washed with a saturated aqueous solution of sodium chloride and dried. After evaporation of the solvent, the resulting residue was subjected to column chromatography through 10 g of silica gel eluted with a 10–15% v/v solution of ethyl acetate in benzene, to give 237 mg (yield 77%) of the desired product as a yellow oil.

Elemental analysis—Calculated for $C_{23}H_{35}N_3O_6S_3Si$: C, 48.14%; H, 6.15%; N, 7.32%; S, 16.76%. Found: C, 48.35%; H, 6.11%; N, 7.14%; S, 16.59%.

Infrared Absorption Spectrum $(CHCl_3)\nu_{max}cm^{-1}$: 3460, 3420, 1780, 1735.

Nuclear Magnetic Resonance Spectrum $(CDCl_3)\delta$ ppm: 0.08 (6H, singlet); 0.85 (9H, singlet); 1.15 (3H, doublet, J=6 Hz); 1.34 (3H, doublet, J=7 Hz); 3.13 (1H, triplet, J=3 Hz); 3.43 (2H, triplet, J=7 Hz); about 4.2 (2H, multiplet); 5.16 (2H, singlet); 5.38 (1H, broad triplet, J=7 Hz); 5.62 (1H, doublet, J=3 Hz); 6.9 (1H, broad singlet); 7.50 (2H, doublet); 8.23 (2H, doublet).

EXAMPLE 2

(3S, 4R)-3-[(R)-1-t-Butyldimethylsilyloxyethyl]-1-[1-hydroxy-1-(p-nitrobenzyloxycarbonyl)methyl]-4-[1-methyl-2-p-nitrobenzyloxycarbonylaminoethylthio(thiocarbonyl)]thioazetidin-2-one A mixture of 230 mg (0.40 mmole) of (3S, 4R)-3-[(R)-1-t-butyldimethylsilyloxyethyl]-4-[1-methyl-2-p-nitrobenzyloxycarbonylaminoethylthio(thiocarbonyl)]-thioazetidin-2-one, 182 mg (0.80 mmole) of p-nitrobenzyl glyoxylate hydrate and 5 ml of benzene was heated under reflux for 10 hours. After completion of the reaction the solvent was distilled off and the resulting residue was subjected to column chromatography through 10 g of silica gel eluted with a 7–10% v/v solution of ethyl acetate in benzene to afford 234 mg (yield 75%) of the desired product as a yellow oil.

Elemental analysis—Calculated for $C_{32}H_{42}N_4O_{11}S_3Si$: C, 49.09%; H, 5.41%; N, 7.16%; S, 12.28%. Found: C, 49.23%; H, 5.38%; N, 7.02%; S, 12.05%.

Infrared Absorption Spectrum $(CHCl_3)\nu_{max}cm^{-1}$: 3530, 3450, 1782, 1760, 1736.

Nuclear Magnetic Resonance Spectrum $(CDCl_3)\delta$ ppm: 0.05 (3H, singlet); 0.08 (3H, singlet); 0.85 (9H, singlet); 1.18 (3H, doublet, J=6 Hz); 1.36 (3H, doublet, J=7 Hz); 3.4 (3H, multiplet); 4.2 (3H, multiplet); 5.1–5.7 (6H, multiplet); 6.2 (1H, multiplet); 7.50 (2H, doublet); 7.55 (2H, doublet); 8.23 (4H, doublet).

EXAMPLE 3

(3S, 4R)-3-[(R)-1-t-Butyldimethylsilyloxyethyl]-4-[1-methyl-2-p-nitrobenzyloxycarbonylaminoethylthio(thiocarbonyl)]thio-1-[1-(p-nitrobenzyloxycarbonyl)triphenylphosphoranylidenemethyl]azetidin-2-one In 5 ml of tetrahydrofuran were dissolved 223 mg (0.285 mmole) of (3S, 4R)-3 -[(R)-1-t-butyldimethylsilyloxyethyl]-1-[1-hydroxy-1-(p-nitrobenzyloxycarbonyl)methyl]-4-[1-methyl-2-p-nitrobenzyloxycarbonylaminoethylthio(thiocarbonyl)]thioazetidin-2-one. To the resulting solution were added, in turn, 34 mg (0.31 mmole) of 2,6-lutidine and 37 mg (0.31 mmole) of thionyl chloride at 31 15° C. The mixture was stirred at that temperature for 15 minutes. After the addition of a further 60 mg (0.56 mmole) of 2,6-lutidine and 183 mg (0.70 mmole) of triphenylphosphine, the mixture was stirred at 65° C. in a stream of nitrogen for 35 hours. Upon completion of the reaction, the mixture was diluted with ethyl acetate, washed with water and dried. The solvent was distilled off and the resulting residue was subjected to column chromatography through 10 g of silica gel eluted with a 15–20% v/v solution of ethyl acetate in benzene to give 159 mg (yield 54% ) of the desired product as a yellow oil.

Elemental analysis—Calculated for $C_{50}H_{55}N_4O_{10}PS_3Si$: C, 58.46%; H, 5.40%; N, 5.45%; P, 3.01%. Found: C, 58.19%; H, 5.51%; N, 5.28%; P, 2.86%.

Infrared Absorption Spectrum $(CHCl_3)$ $\nu_{max}cm^{-1}$: 3450, 1760, 1734, 1623.

EXAMPLE 4 p-Nitrobenzyl (5R, 6S)-6-[(R)-1-t-butyldimethylsilyloxyethyl]-2-(1-methyl-2-p-nitrobenzyloxycarbonylaminoethylthio)penem-3-carboxylate and its (5S)-isomer A mixture of 155 mg of (3S, 4R)-3-[(R)-1-t-butyldimethylsilyloxyethyl]-4-[1-methyl-2-p-nitrobenzyloxycarbonylaminoethylthio(thiocarbonyl)]thio-1-[1-(p-nitrobenzyloxycarbonyl)triphenylphosphoranylidenemethyl]azetidin-2-one, 10 mg of hydroquinone and 15 ml of xylene was heated under reflux at 130° C. in a stream of nitrogen for 7.5 hours. After completion of the reaction, the solvent was distilled off under reduced pressure and the resulting residue was subjected to preparative thin layer chromatography on silica gel developed with a 3:1 by volume mixture of benzene and ethyl acetate to afford 81 mg (yield 73%) of the desired product and 16 mg (yield 14%) of its (5S)-isomer as oils. Both products obtained above were confirmed by NMR to be 1:1 mixtures of stereoisomers owing to the asymmetric carbon atoms of the substituents at the 2-position.

Elemental analysis—Calculated for $C_{32}H_{40}N_4O_{10}S_2Si$: C, 52.44%; H, 5.50%; N, 7.65%; S, 8.75%. Found: C, 52.69%; H, 5.44%; N, 7.38%; S, 8.51% [(5R)-Isomer]. C, 52.55%; H, 5.67%; N, 7.37%; S, 8.54% [(5S)-Isomer].

Infrared Absorption Spectra $(CHCl_3)$ $\nu_{max}cm^{-1}$: 3460, 1798, 1735, 1700 (shoulder)-(5R). 3450, 1798, 1735, 1700 (shoulder)-(5S).

Ultraviolet Absorption Spectra (tetrahydrofuran) $\lambda_{max}$nm: 265 ($\epsilon$,25900), 340 ($\epsilon$,10500)-(5R). 265 ($\epsilon$,25400), 336 ($\epsilon$,9900)-(5S).

Nuclear Magnetic Resonance Spectra (CDCl$_3$)$\delta$ ppm; (5R)-Isomer: 0.03, 0.06 (6H, singlet); 0.83 (9H, singlet); 1.23 (3H, doublet, J=6 Hz); 1.3 (3H, multiplet); 3.45 (3H, multiplet); 3.71, 3.73 (1H, doubled doublet, J=4 and 2 Hz); 4.2 (2H, multiplet); 5.18 (1H, doublet, J=14.5 Hz); 5.17 (2H, singlet); about 5.4 (1H, multiplet); 5.38 (1H, doublet, J=14.5 Hz); 5.61 (1H, broad singlet); 7.48 (2H, doublet); 7.60 (2H, doublet); 8.16 (4H, doublet); (5S)-Isomer: 0.12 (6H, singlet); 0.88 (9H, singlet); 1.40 (6H, doublet, J=6 Hz); about 3.5 (3H, multiplet); 3.87 (1H, doubled doublet, J=10 and 4 Hz); about 4.4 (2H, multiplet); 5.16 (2H, singlet); about 5.3 (1H, multiplet); 5.22 (1H, doublet, J=14.5 Hz); 5.42 (1H, doublet, J=14.5 Hz); 5.61, 5.68 (1H, 1:1, doublet, J=4 Hz); 7.47 (2H, doublet); 7.61 (2H, doublet); 8.18 (4H, doublet).

EXAMPLE 5 p-Nitrobenzyl (5R, 6S)-6-[(R)-1-hydroxyethyl]-2-[1-methyl-2-(p-nitrobenzyloxycarbonylamino)ethylthio]penem-3-carboxylate A mixture of 80 mg (0.109 mmole) of p-nitrobenzyl (5R, 6S)-6-[(R)-1-t-butyldimethylsilyloxyethyl]-2-[1-methyl-2-(p-nitrobenzyloxycarbonylamino)ethylthio]penem-3-carboxylate, 65 mg (1.09 mmole) of acetic acid, 114 mg (0.437 mmole) of tetrabutylammonium fluoride and 4.5 ml of tetrahydrofuran was left to stand at room temperature for 24 hours. At the end of this time, the mixture was diluted with ethyl acetate and washed successively with water and an aqueous solution of sodium bicarbonate. After drying the mixture, the solvent was distilled off and the crystalline residue was washed with ethyl acetate to afford 18 mg (yield 27%) of the desired stereoisomer A melting at 195°-198° C. The washings were concentrated and subjected to thin layer chromatography on silica gel developed with a 3:1 by volume mixture of ethyl acetate and chloroform to give 32 mg (yield 47%) of an oil containing another stereoisomer B as the main component.

The physical data of crystalline isomer A are as follows:

Elemental analysis— Calculated for C$_{26}$H$_{26}$N$_4$O$_{10}$S$_2$: C, 50.48%; H, 4.24%; N, 9.06%; S, 10.37%. Found: C, 50.33%; H, 4.18%; N, 9.13%; S, 10.19%.

Infrared Absorption Spectrum (Nujol-Trade Mark)$\nu_{max}$cm$^{-1}$: 3450, 3290, 1775, 1690.

Specific rotation $[\alpha]_D^{25}=+92.4°$ (c=0.38, tetrahydrofuran).

Nuclear Magnetic Resonance Spectrum (heptadeuterated dimethyl-formamide)$\delta$ ppm: 1.32 (3H, doublet, J=6 Hz); 1.42 (3H, doublet, J=6.5 Hz); about 3.5 (3H, multiplet); 3.95 (1H, doubled doublet, J=7 and 1.5 Hz); about 4.2 (2H, multiplet); 5.28 (2H, singlet); 5.37 (1H, doublet, J=14.5 Hz); 5.65 (1H, doublet, J=14.5 Hz); 5.85 (1H, doublet, J=1.5 Hz); 7.69 (2H, doublet); 7.81 (2H, doublet); 8.27 (4H, doublet).

The following is the Nuclear Magnetic Resonance Spectrum (heptadeuterated dimethylformamide) of the oily isomer B, $\delta$ppm: 1.32 (3H, doublet, J=6 Hz); 1.46 (3H, doublet, J=6.5 Hz); 3.95 (1H, doubled doublet, J=7 and 1.5 Hz); about 4.2 (2H, multiplet); 5.28 (2H, singlet); 5.37 (1H, doublet, J=14.5 Hz); 5.65 (1H, doublet, J=14.5 Hz); 5.87 (1H, doublet, J=1.5 Hz); 7.69 (2H, doublet); 7.81 (2H, doublet); 8.27 (4H, doublet).

EXAMPLE 6

(5R, 6S)-2-(2-Amino-1-methylethylthio)-6-[(R)-1-hydroxyethyl]penem-3-carboxylic acid 46 mg of p-nitrobenzyl (5R, 6S)-2-[1-methyl-2-(p-nitrobenzyloxycarbonylamino)ethylthio]-6-[(R)-1-hydroxyethyl]penem-3-carboxylate (a 1:1 mixture of stereoisomers A and B) (prepared in Example 5) were dissolved in a mixture of 4 ml of tetrahydrofuran and 4 ml of a 0.1 M phosphate buffer solution (pH 7.1). 120 mg of 10% w/w palladium on charcoal were added and then the mixture was stirred under an atmosphere of hydrogen for 5.5 hours. At the end of this time, the reaction mixture was filtered and the catalyst was washed with 4 ml of the phosphate buffer solution mentioned above. The filtrate and the washings were combined and washed with ethyl acetate. The aqueous layer was concentrated to about 4 ml at room temperature under reduced pressure and subjected to chromatography using 15 ml of Diaion HP20AG (a product of Mitsubishi Chemical Industries Co., Ltd.) eluted with a 4–5% v/v mixture of acetone in water. The fractions were collected and lyophilized to give 11.5 mg (yield 51%) of the desired product as a powder.

Ultraviolet Absorption Spectrum (H$_2$O) $\lambda_{max}$nm: 254 ($\epsilon$,4900), 322 ($\epsilon$,6500).

Infrared Absorption Spectrum (KBr) $\nu_{max}$cm$^{-1}$: 3400 (broad), 1767, 1585.

Specific rotation $[\alpha]_D^{25}=+120°$ (c=0.54, H$_2$O).

Nuclear Magnetic Resonance Spectrum (D$_2$O)-tetramethylsilane was used as an external standard-$\delta$ ppm: 1.31 (3H, doublet, J=6 Hz); 1.42, 1.46 (3H, 1:1, doublet, J=7 Hz); 2.8–3.8 (3H, multiplet); 3.96 (1H, doubled doublet, J=6 and 1.5 Hz); 4.3 (1H, multiplet); 5.69, 5.72 (1H, 1:1, doublet, J=1.52 Hz).

EXAMPLE 7

(5R, 6S)-2-(2-Amino-1-methylethylthio)-6-[(R)-1-hydroxyethyl]penem-3-carboxylic acid p-Nitrobenzyl (5R, 6S)-6-[(R)-1-hydroxyethyl]-2-[1-methyl-2-(p-nitrobenzyloxycarbonylamino)ethylthio]penem-3-carboxylate (crystalline isomer A), which has been obtained in Example 5, was subjected to reduction following the same procedure as in Example 6 to remove the protecting group and give the desired amino acid in a 53% yield.

Ultraviolet Absorption Spectrum (H$_2$O)$\lambda_{max}$nm: 251 (5200), 320 (6000).

Infrared Absorption Spectrum (KBr)$\nu_{max}$cm$^{-1}$: 3400, 1770, 1580.

Nuclear Magnetic Resonance Spectrum (D$_2$O) $\delta$ppm: 1.31 (3H, doublet, J=6 Hz); 1.42 (3H, doublet, J=7 Hz); 2.8–3.8 (3H, multiplet); 3.96 (1H, doubled doublet, J=6 and 1.5 Hz); 4.3 (1H, multiplet); 5.69 (1H, doublet, J=1.52 Hz).

EXAMPLE 8

(3S, 4R)-3-[(R)-1-t-Butyldimethylsilyloxyethyl]-4-[2-(p-nitrobenzyloxycarbonylamino)propylthio(thiocarbonyl)]thioazetidin-2-one Following the same procedure as described in Example 1, but reacting sodium trithiocarboxylate [which has been prepared from 2-methyl-2-(p-nitrobenzyloxycarbonylamino)propanethiol and carbon disulphide] with (3R, 4R)-4-acetoxy-3-[(R)-1-t-butyldimethylsilyloxyethyl]azetidin-2-one, there was obtained the desired product as a yellow oil in an 80% yield.

Infrared Absorption Spectrum $(CHCl_3)\nu_{max}cm^{-1}$: 3450, 3420, 1780, 1735.

EXAMPLE 9

(3S, 4R)-3-[(R)-1-t-Butyldimethylsilyloxyethyl]-1-[1-hydroxy-1-(p-nitrobenzyloxycarbonyl)methyl]-4-[2-(p-nitrobenzyloxycarbonylamino)-propythio(thiocarbonyl)]thioazetidin-2-one Following the procedure described in Example 2, the title compound was obtained in an 87% yield from (3S, 4R)-3-[(R)-1-t-butyl dimethylsilyloxyethyl]-4-[2-(p-nitrobenzyloxycarbonylamino)propylthio(thiocarbonyl)]thioazetidin-2-one.

Infrared Absorption Spectrum $(CHCl_3)\nu_{max}cm^{-1}$: 3530, 3450, 1780, 1760, 1740.

EXAMPLE 10

(3S, 4R)-[(R)-1-t-Butyldimethylsilyloxyethyl]-4-[2-(p-nitrobenzyloxycarbonylamino)propylthio(thiocarbonyl)]thio-1-[1-(p-nitrobenzyloxycarbonyl)triphenylphosphoranylidenemethyl]azetidin-2-one Following the procedure described in Example 3, the title compound was obtained in a 60% yield from (3R, 4R)-3-[(R)-1-t-butyldimethylsilyloxyethyl]-1-[1-hydroxy-1-(p-nitrobenzyloxycarbonyl)methyl]-4-[2-(p-nitrobenzyloxycarbonylamino)propylthio(thiocarbonyl)]thioazetidin-2-one.

Infrared Absorption Spectrum $(CHCl_3)\nu_{max}cm^{-1}$: 3450, 1760, 1735, 1625.

EXAMPLE 11 p-nitrobenzyl (5R, 6S)-6-[(R)-1-t-butyldimethylsilyloxyethyl]-2-[2-(p-nitrobenzyloxycarbonylamino)propylthio]penem-3-carboxylate and its (5S)-isomer Following the procedure described in Example 4, (3S, 4R)-[(R)-1-t-butyldimethylsilyloxyethyl]-4-[2-(p-nitrobenzyloxycarbonyl)propylaminothio(thiocarbonyl)]thio-1-[1-(p-nitrobenzyloxycarbonyl)triphenylphosphoranylidenemethyl]azetidin-2-one was heated in xylene to afford the desired trans-isomer (yield 70%) and its (5S)-cis-isomer (yield 14%).

Infrared Absorption Spectrum $(CHCl_3)\nu_{max}cm^{-1}$: 3440, 1790, 1725, 1702-(5R). 3430, 1785, 1722, 1700-(5S).

Nuclear Magnetic Resonance Spectrum $(CDCl_3)\delta ppm$: (5R)-Isomer: 0.04 (3H, singlet); 0.07 (3H, singlet); 0.79 (9H, singlet); 1.16 (3H, doublet, J=6 Hz); 1.24 (3H, doublet, J=6.5 Hz); 3.19 (9H, doublet, J=6.5 Hz); 3.60–3.75 (1H, multiplet); 3.85–4.45 (2H, multiplet); 5.03 (1H, doublet, J=8.5 Hz); 5.19 (2H, singlet); 5.23, 5.40 (2H, AB quartet, J=14 Hz); 5.65 (1H, doublet, J=1.8 Hz); 7.50 (2H, doublet); 7.65 (2H, doublet); 8.22 (4H, doublet). (5S)-Isomer: 0.12 (6H, singlet); 0.83 (9H, singlet); 1.31 (3H, doublet, J=6 Hz); 1.42 (3H, doublet, J=6 Hz); 3.18 (2H, doublet, J=6 Hz); 3.87 (1H, doubled doublet, J=10 and 4 Hz); 3.9–4.5 (2H, multiplet); 4.99 (1H, doublet, J=8 Hz); 5.16 (2H, singlet); 5.22, 5.42 (2H, AB quartet, J=14 Hz); 5.68 (1H, doublet, J=4 Hz); 7.47 (2H, doublet); 7.61 (2H, doublet); 8.18 (4H, doublet).

EXAMPLE 12 p-Nitrobenzyl (5R, 6S)-6-[(R)-1-hydroxyethyl]-2-[2-(p-nitrobenzyloxycarbonylamino)propylthio]penem-3-carboxylate Following the procedure described in Example 6, p-nitrobenzyl (5R, 6S)-6-[(R)-1-t-butyldimethylsilyloxyethyl]-2-[2-(p-nitrobenzyloxycarbonylamino)propylthio]penem-3-carboxylate was subjected to removal of the silyl group, giving the desired product in an 80% yield.

Ultraviolet Absorption Spectrum (ethanol)$\lambda_{max}$nm: 264, 338.

Infrared Absorption Spectrum $(CHCl_3)\nu_{max}cm^{-1}$: 3430, 1790, 1730, 1700.

Nuclear Magnetic Resonance Spectrum (heptadeuterated dimethylformamide) $\delta ppm$: 1.29 (6H, doublet, J=6.5 Hz); 3.25 (2H, doublet, J=6 Hz); 3.7–4.5 (3H, multiplet); 5.30 (2H, singlet); 5.42, 5.60 (2H, AB quartet, J=14 Hz); 5.91 (1H, doublet, J=1.5 Hz); 7.53 (1H, doublet, J=9 Hz); 7.73 (2H, doublet); 7.87 (2H, doublet); 8.34 (4H, doublet).

EXAMPLE 13

(5R, 6S)-2-(2-Aminopropylthio)-6-[(R)-1-hydroxyethyl]-penem-3-carboxylic acid

Following the procedure described in Example 7, p-nitrobenzyl (5R, 6S)-6-[(R)-1-hydroxyethyl]-2-[2-(p-nitrobenzyloxycarbonylamino)propylthio]penem-3-carboxylate was reduced, affording the desired amino acid in a 55% yield.

Ultraviolet Absorption Spectrum $(H_2O)\lambda_{max}$nm: 252($\epsilon$, 4600), 320($\epsilon$, 5700).

Infrared Absorption Spectrum $(KBr)\nu_{max}cm^{-1}$: 3400, 1770, 1570.

Nuclear Magnetic Resonance Spectrum $(D_2O)\delta ppm$: 1.31 (3H, doublet, J=6.5 Hz); 1.41 (3H, doublet, J=6.5 Hz); 2.8–3.3 (2H, multiplet); 3.5 (1H, multiplet); 3.95 (1H, doubled doublet, J=6 and 1.8 Hz); 4.3 (1H, multiplet); 5.69 ($\frac{1}{2}$H, doublet, J=1.8 Hz); 5.72 ($\frac{1}{2}$H, doublet, J=1.8 Hz).

EXAMPLE 14

(3S, 4R)-3-[(R)-1-t-Butyldimethylsilyloxyethyl]-4-[(R)-1-methyl-2-(p-nitrobenzyloxycarbonylamino)ethylthio(-thiocarbonyl)]thioazetidin-2-one To a solution of sodium (518 mg, 22.5 mmole) in methanol (100 ml) was added at $-10°$ C. (R)-1-methyl-2-(p-nitrobenzyloxycarbonylamino)ethanethiol (6.61 g, 23.1 mmole). The mixture was stirred for 5 minutes, and then carbon disulphide (1.76 g, 23.1 mmole) was added and stirring was continued for a further 10 minutes. (3R, 4R)-4-acetoxy-3-[(R)-1-t-butyldimethylsilyloxyethyl]azetidin-2-one (6.46 g, 22.5 mmole) was then added at the same temperature, after which the bath temperature was raised to 0° C. over about 1 hour. About 300 mg of acetic acid was then added, and the reaction mixture was diluted with ethyl acetate and washed with a saturated aqueous solution of sodium chloride. After the solution had been dried, the solvent was distilled off under reduced pressure and the residue was purified through column chromatography (200 g of silica gel), eluted with a 10% v/v solution of ethyl acetate in benzene, affording the desired compound (10.8 g, 84%) in the form of a yellow oil.

Elemental analysis—Calculated for $C_{23}H_{55}O_6S_3Si$: C, 48.14%; H, 6.15%; N, 7.32%; S, 16.76%. Found: C, 48.22%; H, 6.12%; N, 7.18%; S, 16.55%.

Infrared Absorption Spectrum $(CHCl_3)\nu_{max}cm^{-1}$: 3460, 3420, 1780, 1735.

Nuclear Magnetic Resonance Spectrum $(CDCl_3)\delta$ ppm: 0.08 (6H, singlet); 0.85 (9H, singlet); 1.15 (3H, doublet, J=6 Hz); 1.34 (3H, doublet, J=7 Hz); 3.13 (1H, triplet, J=3 Hz); 3.43 (2H, triplet, J=7 Hz); about 4.2 (2H, multiplet); 5.16 (2H, singlet); 5.38 (1H, broad triplet, J=7 Hz); 5.62 (1H, doublet, J=3 Hz); 6.9 (1H, broad singlet); 7.50 (2H, doublet); 8.23 (2H, doublet).

EXAMPLE 15

(3S, 4R)-3-[(R)-1-t-Butyldimethylsilyloxyethyl]-1-[1-hydroxy-1-(p-nitrobenzyloxycarbonyl)methyl]-4-[(R)-1-methyl-2-(p-nitrobenzyloxycarbonylamino)ethylthio(thiocarbonyl)]thioazetidin-2-one (3S, 4R)-3-[(R)-1-t-Butyldimethylsilyloxyethyl]-4-[(R)-1-methyl-2-(p-nitrobenzyloxycarbonylamino)ethylthio(thiocarbonyl)]thioazetidin-2-one (10.8 g, 18.8 mmole) and p-nitrobenzyl glyoxylate hydrate (8.53 g, 37.6 mmole) were refluxed in benzene (100 ml) for 20 hours. After completion of the reaction, the solvent was distilled off under reduced pressure and the residue was purified by column chromatography (150 g of silica gel), eluted first with a 15% v/v solution of acetone in hexane, giving some unchanged starting compound (1.62 g, 15%), and then with a 30% v/v solution of acetone in hexane, giving the desired compound (12.6 g, 85%) in the form of a yellow oil.

Elemental analysis—Calculated for $C_{32}H_{42}N_4O_{11}S_3Si$: C, 49.09%; H, 5.41%; N, 7.16%; S, 12.28%. Found: C, 49.15%; H, 5.38%; N, 6.91%; S, 12.07%.

Infrared Absorption Spectrum $(CHCl_3)\nu_{max}cm^{-1}$: 3530, 3450, 1782, 1760, 1736.

Nuclear Magnetic Resonance Spectrum $(CDCl_3)\delta$ ppm: 0.05 (3H, singlet); 0.08 (3H, singlet); 0.85 (9H, singlet); 1.18 (3H, doublet, J=6 Hz); 1.36 (3H, doublet, J=7 Hz); 3.4 (3H, multiplet); 4.2 (3H, multiplet); 5.1 — 5.7 (6H, multiplet); 6.2 (1H, multiplet); 7.50 (2H, doublet); 7.55 (2H, doublet); 8.23 (4H, doublet).

EXAMPLE 16

(3S, 4R)-3-[(R)-1-t-Butyldimethylsilyloxyethyl]-4-[(R)-1-methyl-2-(p-nitrobenzyloxycarbonylamino)ethylthio(-thiocarbonyl)]thio-1-[1-(p-nitrobenzyloxycarbonyl)triphenylphosphoranylidenemethyl]azetidin-2-one To a solution of (3S, 4R)-3-[(R)-1-t-butyldimethylsilyloxyethyl]-1-[1-hydroxy-1-(p-nitrobenzyloxycarbonyl)methyl]-4-[(R)-1-methyl-2-(p-nitrobenzyloxycarbonylamino)ethylthio(thiocarbonyl)]thioazetidin-2-one (12.6 g, 16.1 mmole) in tetrahydrofuran (150 ml) were added at −15° C., in turn, 2,6-lutidine (2.00 g, 18.7 mmole) and thionyl chloride (2.11 g, 17.7 mmole), and the mixture was stirred at the same temperature for 15 minutes. 2,6-Lutidine (3.45 g, 32.2 mmole) and triphenylphosphine (12.6 g, 48.1 mmole) were then added and the mixture was stirred at 65° C. under a nitrogen stream for a further 35 hours. After completion of the reaction, the reaction mixture was diluted with ethyl acetate; washed with water and dried. The solvent was distilled off under reduced pressure and the residue was purified by column chromatography (250 g of silica gel); eluted with a 15-20% v/v solution of ethyl acetate in benzene; giving the desired compound (10.9 g; 66%) in the form of a yellow oil.

Elemental analysis—Calculated for $C_{50}H_{55}N_4O_{10}PS_3Si$: C, 58.46%; H, 5.40%; N, 5.45%; S, 3.01%. Found: C, 58.59%; H, 5.22%; N, 5.33%; S, 2.95%.

Infrared Absorption Spectrum $(CHCl_3)\nu_{max}cm^{-1}$: 3450, 1760, 1734, 1623.

EXAMPLE 17 p-Nitrobenzyl (5R, 6S)-6-[(R)-1-t-butyldimethylsilyloxyethyl]-2-[(R)-1-methyl-2-(p-nitrobenzyloxycarbonylamino)ethylthio]-penem-3-carboxylate and its (5S)-isomer.

(3S, 4R)-3-[(R)-1-t-Butyldimethylsilyoxyethyl]-4-[(R)-1-methyl-2-(p-nitrobenzyloxycarbonylamino)ethylthio(thiocarbonyl)]thio-1-[1-(p-nitrobenzyloxycarbonyl)triphenylphosphoranylidenemethyl]azetidin-2-one (9.90 g) and hydroquinone (570 mg) were heated in xylene (1000 ml) at 127°-130° C. under a nitrogen stream for 13.5 hours. After completion of the reaction, the solvent was distilled off under reduced pressure and the residue was purified by column chromatography through 150 g of silica gel, first eluted with a 5% v/v solution of ethyl acetate in benzene, giving the cis-isomer [(5S, 6S)-isomer, 1.60 g, 23%] in the form of an oil, and then eluted with a 5-10% v/v solution of ethyl acetate in benzene, giving the trans-isomer [(5R, 6S)-isomer, 5.24 g, 74%] which was recrystallized from benzene, affording the pure product melting at 163°-164° C.

Elemental analysis—Calculated for $C_{32}H_{40}N_4O_{10}S_2Si$: C, 52.44%; H, 5.50%; N, 7.65%; S, 8.75%. Found: C, 52.70%; H, 5.39%; N, 7.43%; S, 8.55% (trans-isomer). C, 52.58%; H, 5.44%; N, 7.41%; S, 8.52% (cis-isomer).

Infrared Absorption Spectra: trans-isomer $(KBr)\nu_{max}cm^{-1}$: 3400 (broad), 1785, 1735, 1690. cis-isomer $(CHCl_3)\nu_{max}cm^{-1}$: 3450, 1798, 1735, 1700 (shoulder).

Specific rotation $[\alpha]_D^{25} = +29.6°$ (c=0.47, $CHCl_3$)(trans-isomer).

Nuclear Magnetic Resonance Spectra $(CDCl_3)\delta$ ppm: trans-isomer: 0.03, 0.06 (6H, singlet); 0.83 (9H, singlet); 1.23 (3H, doublet J=6 Hz); about 1.3 (3H, multiplet); 3.45 (3H, multiplet); 3.71 (1H, doubled doublet, J=4 and 1.5 Hz); 4.2 (2H, multiplet); 5.17 (2H, singlet); 5.18 (1H, doublet, J=14.5 Hz); 5.38 (1H, doublet, J=14.5 Hz); about 5.4 (1H, multiplet); 5.61 (1H, doublet, J=1.5 Hz); 7.48 (2H, doublet); 7.60 (2H, doublet); 8.16 (4H, doublet). cis-isomer: 0.12 (6H, singlet); 0.88 (9H, singlet); 1.40 (6H, doublet, J=6 Hz); about 3.5 (3H, multiplet); 3.87 (1H, doubled doublet, J=10 and 3.5 Hz); about 4.4 (2H, multiplet); 5.16 (2H, singlet); about 5.3 (1H, multiplet); 5.22 (1H, doublet, J=14.5 Hz); 5.42 (1H, doublet J=14.5 Hz); 5.61 (1H, doublet, J=3.5 Hz); 7.47 (2H, doublet); 7.61 (2H, doublet); 8.18 (4H, doublet).

EXAMPLE 18 p-Nitrobenzyl (5R, 6S)-6-[(R)-1-hydroxyethyl]-2-[(R)-1-methyl-2-(p-nitrobenzyloxycarbonylamino)ethylthio]penem-3-carboxylate A solution of p-nitrogenzyl (5R, 6S)-6-[(R)-1-t-butyldimethylsilyloxyethyl]-2-[(R)-1-methyl-2-(p-nitrobenzyloxycarbonylamino)ethylthio]penem-3-carboxylate (3.39 g, 4.63 mmole), acetic acid (2.78 g, 46 mmole) and tetrabutylammonium fluoride (3.62 g, 13.9 mmole) in tetrahydrofuran (66 ml) was stirred at room temperature for 15 hours. After completion of the reaction, the reaction mixture was diluted with ethyl acetate and washed, in turn, with water and an aqueous solution of sodium bicarbonate. The solvent was distilled off under reduced pressure and the resulting crystalline residue was recrystallized from ethyl acetate, affording the desired compound (1.98 g) melting at 158°–160° C. The filtrate was subjected to column chromatography, affording a further 0.36 g of crystals of the desired compound melting at 158°–160° C. The overall yield was 2.43 g (82%).

The Nuclear Magnetic Resonance Spectrum of the compound was in full agreement with that of isomer B in Example 5.

Elemental analysis—Calculated for $C_{26}H_{26}N_4O_{10}S_2$: C, 50.48%; H, 4.24%; N, 9.06%; S, 10.37%. Found: C, 50.42%; H, 4.19%; N, 8.95%; S, 10.33%.

Infrared Absorption Spectrum (KBr) $\nu_{max}$cm$^{-1}$: 3520, 3330, 1780, 1710.

Specific rotation $[\alpha]_{25}{}^D = +70.0°$ (c=0.47, dimethylformamide).

EXAMPLE 19

(5R, 6S)-2-[(R)-2-amino-1-methylethylthio]-6-[(R)-1-hydroxyethyl]-penem-3-carboxylic acid A solution of p-nitrobenzyl (5R, 6S)-6-[(R)-1-hydroxyethyl]-2-[(R)-1-methyl-2-(p-nitrobenzyloxycabonylamino)ethylthio]penem-3-carboxylate (2.19 g) in tetrahydrofuran (200 ml) and 0.1 M phosphate buffer solution (pH 7.1, 200 ml) was stirred under a hydrogen stream for 5 hours in the presence of 4 g of 10% w/w palladium on charcoal. After completion of the reaction, the reaction mixture was filtered, the catalyst was washed with 0.1 M phosphate buffer solution (50 ml), and the filtrate and the washings were combined. The solution was washed twice with ethyl acetate and then the aqueous layer was concentrated to about 200 ml by evaporation at room temperature under reduced pressure. The concentrate was purified by column chromatography (Diaion HP20AG, 50 ml), eluted with a 5% v/v solution of acetone in water and the eluate was lyophilized. The powdery substance thus obtained was again chromatographed, thus giving the desired compound (604 mg, 56%) in the form of a colourless powder.

Infrared Absorption Spectrum (KBr) $\nu_{max}$cm$^{-1}$: 3400 (broad), 1775, 1580.

Specific rotation $[\alpha]_D{}^{25} = +143.4°$ (c=0.47, H$_2$O).
Nuclear Magnetic Resonance Spectrum (D$_2$O) δppm: 1.31 (3H, doublet, J=6 Hz); 1.46 (3H, doublet J=7 Hz); 3.1–3.8 (3H, multiplet); 3.96 (1H, doubled doublet, J=6 and 1.5 Hz); 4.26 (1H, multiplet); 5.69 (1H, doublet, J=1.5 Hz).

EXAMPLE 20

(5R, 6S)-2-[(R)-2-formimidoylamino-1-methylethylthio]-6-[(R)-1-hydroxyethyl]penem-3-carboxylic acid To a solution of (5R, 6S)-2-[(R)-2-amino-1-methylethylthio]-6-[(R)-1-hydroxyethyl]penem-3-carboxylic acid (50 mg, 0.16 mmole) in a 0.1 M phosphate buffer solution (pH 7.1; 10ml) was added, with stirring and under ice-cooling, dropwise a 2 N aqueous solution of sodium hydroxide to adjust the pH to 8.5. To the solution was then added in small portions methyl formimidate hydrochloride (236 mg, 2.47 mmole) over 5 minutes, while maintaining the pH at 8.5 by adding a 2 N aqueous solution of sodium hydroxide dropwise. After stirring for 5 minutes, the solution was adjusted to pH 7.0 by the addition of 2 N aqueous hydrochloric acid. The solution was purified by column chromatography (Diaion HP20AG, 20 ml). After inorganic salts and impurities had been eluted, the fractions eluted with 3–5% v/v solutions of acetone in water were collected and lyophilized, giving the desired compound (17 mg, 31%) in the form of a colourless powder.

Infrared Absorption Spectrum (KBr) $\nu_{max}$cm$^{-1}$: 3400 (broad), 1770, 1720 (shoulder), 1580.

Specific rotation $[\alpha]_D{}^{25} = +124.1°$ (c=0.34, H$_2$O).
Nuclear Magnetic Resonance Spectrum (D$_2$O) δppm: 1.30 (3H, doublet, J=6 HZ); 1.34 (3H, doublet, J=7 Hz); 3.2–3.7 (3H, multiplet); 3.90 (1H, doubled doublet, J=6 and 1.5 Hz); 4.26 (1H, multiplet); 5.72 (1H, doublet, J=1.5 Hz); 7.83 (1H, singlet).

EXAMPLE 21 p-Nitrobenzyl (5R, 6S)-6-[(R)-1-t-butyldimethylsilyloxyethyl]-2-[(R)-1-methyl-2-(p-nitrobenzyloxycarbonylamino)ethylthio]penem-3-carboxylate A solution of (3S, 4R)-3-[(R)-1-t-butyldimethylsilyloxyethyl]-4-[(R)-1-methyl-2-(p-nitrobenzyloxycarbonylamino)ethylthiothiocarbonyl)]-thio-1-(p-nitrobenzyloxyoxalyl)azetidin-2-one (374 mg, 0.48 mmole) and trimethyl phosphite (475 mg, 3.83 mmole) in dioxan (40 ml) was stirred at 75° C. under a nitrogen stream for 91 hours. The solvent was distilled off under reduced pressure and the residue was purified by preparative thin layer chromatography, eluted with a 1:2 by volume mixture of benzene and ethyl acetate, and then further purified by preparative thin layer chromatography, eluted with a 8:1 by volume mixture of chloroform and ethyl acetate, giving the desired compound (92 mg, 26%). The compound was recrystallized from benzene, affording the pure substance melting at 163°–164° C. The physicochemical data of the compound was in full agreement with those of the compound obtained in Example 17.

PREPARATION 1

(3S, 4R)-3-[(S)-1-Hydroxyethyl]-1-(1-methoxycarbonyl-2-methylprop-1-enyl)-4-methylthioazetidin-2-one In 20 ml of tetrahydrofuran were dissolved (3S, 4R-3-bromo-1-(1-methoxycarbonyl-2-methylprop-1-enyl)-4-methylthioazetidin-2-one (1.96 g, 6.38 mmole) and acetaldehyde (843 mg, 3 equivalents). The resulting solution was added to a solution of zinc (625 mg, 1.5 equivalents) and diethylaluminium chloride (6.68 ml, 1.5 equivalents, 15% w/v hexane solution) in 15 ml of tetrahydrofuran, with stirring at 15°–20° C. over a period of 40 minutes, and then the mixture was stirred for a further 1 hour. The mixture was diluted with, in turn, water and ethyl acetate. The white precipitate produced was filtered off using a Celite (Trade Mark) filter aid and the filtrate was extracted with ethyl acetate. The extract was treated by a conventional method to afford 2.05 g of the crude product as an oil, which was subjected to column chromatography through silica gel (about 30 g) developed with a 5:1 by volume mixture of chloroform and ethyl acetate to give 1.04 g (yield 60%) of the desired product as a colourless oil. The product was a 4:1 mixture of isomers having the 1′S- and 1′R-configurations on the side chain at the 3-position.

Elemental analysis—Calculated for $C_{12}H_{19}O_4NS$: C, 52.74%; H, 6.96%; N, 5.13%; S, 11.72%. Found: C, 52.81%; H, 7.21%; N, 5.43%; S, 11.78%.

Infrared Absorption Spectrum (liquid film) $\nu_{max}cm^{-1}$: 3450, 1760, 1710, 1380, 1360, 1225.

Nuclear Magnetic Resonance Spectrum $(CDCl_3)\delta$ppm: 1′S-Isomer: 1.30 (3H, doublet, J=6 Hz); 1.93 (3H, singlet); 2.05 (3H, singlet); 3.14 (1H, doubled doublet, J=6 and 3 Hz); 3.72 (3H, singlet); 4.12 (1H, multiplet); 4.92 (1H, doublet, J=3 Hz). 1′R-Isomer: 1.26 (3H, doublet, J=6 Hz); 1.93 (3H, singlet); 2.05 (3H, singlet); 2.16 (3H, singlet); 3.14 (1H, doubled doublet, J=6 and 3 Hz); 3.72 (3H, singlet); 4.12 (1H, multiplet); 5.04 (1H, doublet, J=3 Hz).

PREPARATION 2

(3S, 4R)-3-[(R)-1-Benzoyloxyethyl]-1-(1-methoxycarbonyl-2-methylprop-1-enyl)-4-methylthioazetidin-2-one In 2 ml of tetrahydrofuran were dissolved (3S, 4R)-3-[(S)-1-hydroxyethyl]-1-(1-methoxycarbonyl-2-methylprop-1-enyl)-4-methylthioazetidin-2-one (105 mg, 0.38 mmole), triphenylphosphine (201 mg, 2 equivalents) and benzoic acid (94 mg, 2 equivalents). To the resulting solution was added little by little a solution of diethyl azodicarboxylate (134 mg, 2 equivalents) in tetrahydrofuran (1 ml) at 20° C. over 10 minutes and then the mixture was stirred at the same temperature for 1.5 hours. The solvent was then distilled off and the residue was dissolved in 3 ml of a 6:1 by volume mixture of benzene and ethyl acetate and left to stand in a refrigerator. The resulting precipitate was filtered off and the filtrate was subjected to thin layer chromatography developed with a 5:1 by volume mixture of benzene and ethyl acetate to afford 119 mg (yield 82%) of the desired product as an oil, containing a small amount of the 1′S-isomer.

Elemental analysis—Calculated for $C_{19}H_{23}NO_5S$: C, 60.48%; H, 6.10%; N, 3.71%; S, 8.49%.

Found: C, 59.20%; H, 6.36%; N, 3.52%; S, 8.68%.

Infrared Absorption Spectrum (liquid film) $\nu_{max}cm^{-1}$: 1765, 1720, 1380, 1360, 1270.

Nuclear Magnetic Resonance Spectrum $(CDCl_3)$ δppm: Main product (1′R-isomer): 1.49 (3H, doublet, J=6 Hz); 1.95 (3H, singlet); 2.03 (3H, singlet); 2.17 (3H, singlet); 3.33 (1H, doubled doublet, J=7 and 3 Hz); 3.74 (3H, singlet); 5.14 (1H, doublet, J=3 Hz); 5.63 (1H, doubled quartet, J=7 and 6 Hz); 7.54 (3H, multiplet); 8.10 (2H, multiplet). By-product (1′S-isomer): 1.52 (3H, doublet, J=6 Hz); 1.95 (3H, singlet); 2.03 (3H, singlet); 2.17 (3H, singlet); 3.33 (1H, doubled doublet, J=7 and 3 Hz); 3.74 (3H, singlet); 4.96 (1H, doublet, J=3 Hz); 5.63 (1H, doubled quartet, J=7 and 6 Hz); 7.54 (3H, multiplet); 8.10 (2H, multiplet).

PREPARATION 3

(3S,4R)-3-[(R)-1-Hydroxyethyl]-1-(1-methoxycarbonyl-2-methylprop-1-enyl)-4-methylthioazetidin-2-one 91 mg (0.24 mmole) of (3S, 4R)-3-[(R)-1-benzoyloxyethyl]-1-(1-methoxycarbonyl-2-methylprop-1-enyl)-4-methylthioazetidin-2-one were dissolved in 1 ml of methanol. To the resulting solution was added a solution of 7.17 mg (0.31 mmole) of sodium in 0.65 ml of methanol at 0° C., and then the mixture was stirred at room temperature (18°–20° C.) for 5 hours. After completion of the reaction, the mixture was made slightly acidic by the addition of acetic acid, diluted with 20 ml of ethyl acetate and washed with water. After drying the mixture, the solvent was distilled off. The resulting residue was subjected to preparative thin layer chromatography on silica gel developed with a 2:1 by volume mixture of benzene and ethyl acetate to give 50 mg (yield 74.4%) of the pure product as an oil, which was proved by nuclear magnetic resonance spectroscopy to be an approximately 4:1 mixture of the 1′R- and 1′S-isomers.

Elemental analysis—Calculated for $C_{12}H_{19}NO_4S$: C, 52.74%, H; 6.96%; N, 5.13%; S, 11.72%. Found: C, 53.03%; H, 7.33% N; 4.68%; S, 11.39%.

Infrared Absorption Spectrum (liquid film) $\nu maxcm^{-1}$: 3450 (broad), 1750, 1720.

Nuclear Magnetic Resonance Spectrum $(CDCl_3)$ δppm: Main product (1′R-isomer): 1.26 (3H, doublet, J=6 Hz); 1.93 (3H, singlet); 2.05 (3H, singlet); 2.15 (3H, singlet); 3.10 (1H, doubled doublet, J=6 and 3 Hz); 3.72 (3H, singlet); 4.23 (1H, doubled quartet, J=6 and 6 Hz); 5.03 (1H, doublet, J=3 Hz). By-product (1′S-isomer): 1.29 (3H, doublet, J=6 Hz); 1.93 (3 H, singlet); 2.05 (3H, singlet); 2.15 (3H, singlet); 3.10 (1H, doubled doublet, J=6 and 3 Hz); 3.72 (3H, singlet); 4.23 (1H, doubled quartet, J=6 and 6 Hz); 4.90 (1H, doublet, J=3 Hz).

PREPARATION 4

(3S, 4R)-3-[(R)-1-t-Butyldimethylsilyloxyethyl]-1-(1-methoxycarbonyl-2-methylprop-1-enyl)-4-methylthioazetidin-2-one In 110 ml of dimethylformamide were dissolved 5.69 g (20.8 mmole) of the mixture containing as a main component (3S, 4R)-3-[(R)-1-hydroxyethyl]-1-(1-methoxycarbonyl-2-methylprop-1-enyl)-4-methylthioazetidin-2-one, which had been obtained in Preparation 3, and 2.54 g (37.3 mmole) of imidazole. To the resulting solution were added 5.33 g (35.3 mmole) of t-butyldimethylchlorosilane at 0° C., and then the mixture was stirred at room temperature overnight. After completion of the reaction, the mixture was diluted with 200 ml of benzene and washed with water. After drying the mixture, the solvent was distilled off and the resulting residue was subjected to column chromatography on 10 times its volume of silica gel eluted with a 10:1 by volume mixture of benzene and ethyl acetate, to give 7.95 g (yield 94%) of the desired product as a colourless oil, while 370 mg (yield 6%) of the starting material was recovered. The product was proved by nuclear magnetic resonance spectroscopy to be an approximately 4:1 mixture of the 1'R- and 1'S-configuration isomers on the side chain at the 3-position.

Elemental analysis—Calculated for $C_{18}H_{33}NO_4SSi$: C, 55.81%; H, 8.53%; N, 3.62%; S, 8.29%. Found: C, 55.44%; H, 8.70%; N, 3.42%; S, 8.45%.

Infrared Absorption Spectrum (liquid film) $\nu_{max}cm^{-1}$: 1760, 1720

Nuclear Magnetic Resonance Spectrum (CDCl₃) δppm: Main product (1'R-isomer): 0.10 (6H, singlet); 0.84 (9H, singlet); 1.23 (3H, doublet, J=6 Hz); 1.92 (3H, singlet); 2.05 (3H, singlet); 2.16 (3H, singlet); 3.05 (1H, doubled doublet, J=5 and 3 Hz); 3.71 (3H, singlet); 4.23 (1H, multiplet); 5.09 (1H, doublet, J=3 Hz). By-product (1'S-isomer): 0.10 (6H, singlet); 0.84 (9H, singlet); 1.28 (3H, doublet, J=6 Hz); 1.92 (3H, singlet); 2.05 (3H, singlet); 2.16 (3H, singlet); 3.20 (1H, multiplet); 3.71 (3H, singlet); 4.23 (1H, multiplet); 4.96 (1H, doublet, J=3 Hz).

PREPARATION 5

(3R, 4R)-4-Acetoxy-3-[(R)-1-t-butyldimethylsilyloxyethyl]-1-(1-methoxycarbonyl-2-methylprop-1-enyl)azetidin-2-one In 38 ml of acetic acid were dissolved 3.85 g (9.95 mmole) of the product containing as a main component (3S, 4R)-3-[(R)-1-t-butyldimethysilyloxyethyl]-1-(1-methoxycarbonyl-2-methylprop-1-enyl)-4-methylthioazetidin-2-one, which had been obtained in Preparation 4, and 5.08 g (15.9 mmole) of mercuric acetate. The solution was stirred under a stream of nitrogen at a bath temperature of 95°–100° C. for 20 minutes. After completion of the reaction, the acetic acid was distilled off under reduced pressure. To the resulting white residue was added at 0° C. an approximately 1:1 by volume mixture of water and ethyl acetate, and then the mixture was stirred. The ethyl acetate layer was separated, washed with water and dried. The solvent was distilled off and the resulting residue was subjected to column chromatography through 30 g of silica gel eluted with a 5:1 by volume mixture of benzene and ethyl acetate, to afford 3.50 g (yield 88%) of the desired product as an oil, which was proved by nuclear magnetic resonance spectroscopy to contain a small amount of the 1'S-configuration isomer on the side chain at the 3-position.

Elemental anaylsis—Calculated for $C_{19}H_{33}NO_6Si$; C, 57.14%; H, 8.27%; N, 3.51%. Found: C, 56.80%; H, 8.44%; N, 3.29%.

Infrared Absorption Spectrum (liquid film) $\nu_{max}cm^{-1}$: 1780, 1755, 1725.

Nuclear Magnetic Resonance Spectrum (CDCl₃) δppm: Main product (1'R-isomer): 0.10 (6H, singlet); 0.90 (9H, singlet); 1.32 (3H, doublet, J=6 Hz); 1.94 (3H, singlet); 2.06 (3H, singlet); 2.22 (3H, singlet); 3.23 (1H, doubled doublet, J=6 and 1.5 Hz); 3.80 (3H, singlet); 4.26 (1H, multiplet); 6.32 (1H, doublet, J=1.5 Hz). By-product (1'S-isomer): 0.10 (6H, singlet); 0.90 (9H, singlet); 1.34 (3H, doublet, J=6 Hz); 1.94 (3H, singlet); 2.06 (3H, singlet); 2.22 (3H, singlet); 3.34 (1H, multiplet); 3.80 (3H, singlet); 4.26 (1H, multiplet); 6.25 (1H, doublet, J=1.5 Hz).

PREPARATION 6

(3R, 4R)-4-Acetoxy-3-[(R)-1-t-butyldimethylsilyloxyethyl]azetidin-2-one

In 300 ml of acetone were dissolved 3 g (7.5 mmole) of the product containing as a main component (3R, 4R)-4-acetoxy-3-[(R)-1-t-butyldimethylsilyloxyethyl]-1-(1-methoxycarbonyl-2-methylprop-1-enyl)azetidin-2-one, which had been obtained in Preparation 5. To the solution was added a solution of 6.43 g (30.1 mmole) of sodium metaperiodate and 120 mg of potassium permanganate in a mixture of 150 ml of water and 150 ml of a 0.1 M phosphate buffer solution (pH 7.02) at about 18° C. over 30 minutes, and then the mixture was stirred at that temperature for 4 hours. After completion of the reaction, the precipitate produced was filtered off and about 25 ml of the above buffer solution was added to the filtrate to adjust its pH to a value of 6.8. The acetone was distilled off at a lower temperature under reduced pressure and the residue was extracted with benzene. The benzene layers were collected and dried. The solvent was distilled off to give a crystalline solid, which was recrystallized from hexane to afford 0.934 g (43.3%) of the desired product as needles melting at 104°–106° C.

Elemental analysis—Calculated for $C_{13}H_{25}O_4NSi$: C, 54.32%; H, 8.77%; N, 4.87%; Found: C, 54.04%; H, 8.79%; N, 4.71%.

Infrared Absorption Spectrum (Nujol-trade mark) $\nu_{max}cm^{-1}$: 3175, 1783, 1743.

Specific rotation $[\alpha]_D^{20} = +48.8°$ (c=0.41, CHCl₃).

Nuclear Magnetic Resonance Spectrum (CDCl₃)δppm: 0.07 (6H, singlet); 0.88 (9H, singlet); 1.25 (3H, doublet, J=6.5 Hz); 2.13 (3H, singlet); 3.20 (1H, doubled doublet, J=3.5 and 1.5 Hz); 4.3 (1H, multiplet); 5.98 (1H, doublet, J=1.5 Hz); 7.24 (1H, broad).

PREPARATION 7

(3S, 4R)-3-[(R)-1-t-Butyldimethylsilyloxyethyl]-4-[(R)-1-methyl-2-(p-nitrobenzyloxycarbonylamino)ethylthio(thiocarbonyl)]thio-1-(p-nitrobenzyloxalyl)azetidin-2-one To a solution of (3S, 4R)-3-[(R)-1-t-butyldimethylsilyloxyethyl]-4-[(R)-1-methyl-2-(p-nitrobenzyloxycarbonylamino)ethylthio(thiocarbonyl)]thioazetidin-2-one (326 mg, 0.57 mmole, obtained in Example 14) and triethylamine (172 mg, 1.70 mmole) in methylene chloride (10 ml) cooled at −10° C. was added, with stirring under a nitrogen stream, p-nitrobenzyloxalyl chloride (416 mg, 1.71 mmole). The mixture was stirred at the same temperature for 25 minutes and a phosphate buffer solution (pH 7, 10 ml) was added thereto. The mixture was extracted with chloroform, washed with water and dried. After the solvent had been evaporated off under reduced pressure, the residue was purified by column chromatography through silica gel (5 g), eluted with a 15:1 by volume mixture of benzene and ethyl acetate, affording the desired compound (385 mg, 87%) in the form of an oil.

Infrared Absorption Spectrum (CHCl₃) $\nu_{max}cm^{-1}$: 1815, 1760, 1720, 1607, 1511.

Nuclear Magnetic Resonance Spectrum (CDCl₃) δppm: 0.10 (6H, singlet); 0.83 (9H, singlet); 1.21 (3H, doublet, J=6 Hz); 1.43 (3H, doublet, J=7 Hz); 3.2–3.7 (3H, multiplet); 4.0–4.6 (2H, multiplet); 5.13 (2H, singlet); 5.34 (2H, singlet); 6.70 (1H, doublet, J=4 Hz); 7.43 (2H, doublet); 7.50 (2H, doublet); 8.13 (2H, doublet); 8.17 (2H, doublet).

We claim:
1. Compounds of formula (I):

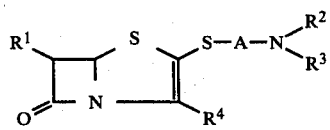 (I)

wherein:
R$^1$ represents a 1-hydroxyethyl group;
R$^2$ represents a hydrogen atom or a C$_1$–C$_2$ alkyl group;
R$^3$ represents a hydrogen atom, a formimidoyl group, or an acetimidoyl group;
A represents an ethylene or trimethylene group having one methyl group in the α-position in its carbon chain; and
R$^4$ represents a carboxy group or a pivaloyloxymethoxycarbonyl group; and pharmaceutically acceptable salts thereof.

2. Compounds as claimed in claim 1, in the form of the sodium or potassium salt.

3. Compounds as claimed in claim 1, wherein the configuration is selected from the (5R,6S) and (5R,6R) configurations.

4. Compounds as claimed in claim 1, wherein R$^1$ represents a 1-hydroxyethyl group, whose α-hydroxy substitutent is in the R configuration.

5. In a pharmaceutical composition comprising an antibiotic and a pharmaceutically acceptable carrier or diluent, the improvement which comprises employing as antibiotic a compound of formula:

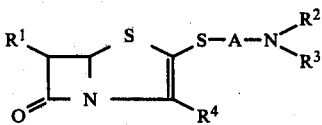 (I)

wherein:
R$^1$ represents a hydroxyalkyl group;
R$^2$ represents a hydrogen atom or a C$_1$–C$_2$ alkyl group;
R$^3$ represents a hydrogen atom, a formimidoyl group or an acetimidoyl group;
A represents an ethylene or trimethylene group having one methyl group in the α-position of the carbon chain; and
R$^4$ represents a carboxy group or a pivaloyloxymethoxycarbonyl group; or a pharmaceutically acceptable salt thereof.

6. 2-(2-Amino-1-methylethylthio)-6-(1-hydroxyethyl)penem-3-carboxylic acid and pharmaceutically acceptable salts thereof.

7. (5R,6S)-(2-Amino-1-methylethylthio)-6-[(R)-1-hydroxyethyl]penem-3-carboxylic acid and pharmaceutically acceptable salts thereof.

8. Compounds as claimed in claim 1, wherein:
R$^1$ represents a 1-hydroxyethyl group,
R$^2$ and R$^3$ represent hydrogen atoms,
A represents an ethylene or trimethylene group having one methyl substituent in its α-position of the carbon chain, and
R$^4$ represents a carboxy group, and pharmaceutically acceptable salts thereof.

* * * * *